US008334237B2

(12) United States Patent
Seitz et al.

(10) Patent No.: US 8,334,237 B2
(45) Date of Patent: Dec. 18, 2012

(54) SUBSTITUTED PHENYLAMIDINES AND THE USE THEREOF AS FUNGICIDES

(75) Inventors: Thomas Seitz, Langenfeld (DE); Klaus Kunz, Düsseldorf (DE); Wahed Ahmed Moradi, Monheim (DE); Jörg Nico Greul, Leichlin-gen (DE); Darren James Mansfield, Kürten (DE); Urlich Heinemann, Leichlingen (DE); Amos Mattes, Langenfeld (DE); Oswald Ort, Leverkusen (DE); Jean-Pierre Vors, Sainte Foy les Lyon (FR); Peter Dahem, Neuss (DE); Ulrike Wachendorff-Neumann, Newied (DE); Arnd Voerste, Köln (DE)

(73) Assignee: Bayer Cropscience AG, Monheim (DE)

( * ) Notice: Subject to any disclaimer, the term of this patent is extended or adjusted under 35 U.S.C. 154(b) by 507 days.

(21) Appl. No.: 12/530,566

(22) PCT Filed: Mar. 8, 2008

(86) PCT No.: PCT/EP2008/001861
§ 371 (c)(1),
(2), (4) Date: Sep. 9, 2009

(87) PCT Pub. No.: WO2008/110312
PCT Pub. Date: Sep. 18, 2008

(65) Prior Publication Data
US 2010/0029588 A1 Feb. 4, 2010

(30) Foreign Application Priority Data

Mar. 12, 2007 (EP) .................................... 07004998

(51) Int. Cl.
*A01N 35/10* (2006.01)
*C07C 257/00* (2006.01)
*C07C 291/00* (2006.01)
*C07C 259/00* (2006.01)

(52) U.S. Cl. ......... 504/344; 564/244; 564/253; 564/256
(58) Field of Classification Search .................. 504/344; 564/244, 253, 256
See application file for complete search history.

(56) References Cited

U.S. PATENT DOCUMENTS

| | | |
|---|---|---|
| 4,192,893 A | 3/1980 | Welle et al. |
| 4,245,432 A | 1/1981 | Dannelly |
| 4,272,417 A | 6/1981 | Barke et al. |
| 4,761,373 A | 8/1988 | Anderson et al. |
| 4,808,430 A | 2/1989 | Kouno |
| 4,863,959 A | 9/1989 | Bentley et al. |
| 5,013,659 A | 5/1991 | Bedbrook et al. |
| 5,084,082 A | 1/1992 | Sebastian |
| 5,141,870 A | 8/1992 | Bedbrook et al. |
| 5,198,599 A | 3/1993 | Thill |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,378,824 A | 1/1995 | Bedbrook et al. |
| 5,434,283 A | 7/1995 | Wong et al. |
| 5,463,175 A | 10/1995 | Barry et al. |
| 5,521,187 A | 5/1996 | Freyne et al. |
| 5,561,236 A | 10/1996 | Leemans et al. |
| 5,576,455 A | 11/1996 | Wang et al. |
| 5,605,011 A | 2/1997 | Bedbrook et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,773,702 A | 6/1998 | Penner et al. |
| 5,776,760 A | 7/1998 | Barry et al. |
| 5,824,790 A | 10/1998 | Keeling et al. |
| 5,840,946 A | 11/1998 | Wong et al. |
| 5,876,739 A | 3/1999 | Turnblad et al. |
| 5,907,975 A | 6/1999 | Giaimo |
| 5,908,810 A | 6/1999 | Donn |
| 5,928,937 A | 7/1999 | Kakefuda et al. |
| 5,965,755 A | 10/1999 | Sernyk et al. |
| 5,969,169 A | 10/1999 | Fan |
| 6,013,861 A | 1/2000 | Bird et al. |
| 6,063,947 A | 5/2000 | DeBonte et al. |
| 6,066,782 A | 5/2000 | Kossmann et al. |

(Continued)

FOREIGN PATENT DOCUMENTS

EP 0 571 427 A1 12/1993

(Continued)

OTHER PUBLICATIONS

International Search Report PCT/EP2008/001861; dated Apr. 25, 2008 (8 pages).
Galat et al., "The interaction of Amides with Amines: A General Method of Acylation," JACS, 1943, 65, p. 1566.
Comai et al., "An Altered aroA Gene Product Confers Resistance to the Herbicide Glyphosate," Science (1983), 221, pp. 370-371.
Barry et al., "Inhibitors of Amino Acid Biosynthesis: Strategies for Imparting Glyphosate Tolerance to Crop Plants," Curr. Topics Plant Physiol. (1992), 7, pp. 139-145.
Shah et al., "Engineering Herbicide Tolerance in Transgenic Plants," Science, (1986), vol. 233, pp. 478-481.

(Continued)

*Primary Examiner* — Sreeni Padmanabhan
*Assistant Examiner* — Sarah Pihonak
(74) *Attorney, Agent, or Firm* — Baker Donelson Bearman, Caldwell & Berkowitz, PC

(57) ABSTRACT

The present invention relates to oxime ether-, hydrazone- or azomethine-substituted phenylamidines of the general formula (I), to a process for their preparation, to the use of the amidines according to the invention for controlling unwanted microorganisms and also to a composition for this purpose, comprising the amidines according to the invention. Furthermore, the invention relates to a method for controlling unwanted microorganisms by applying the compounds according to the invention to the microorganisms and/or their habitat.

14 Claims, No Drawings

U.S. PATENT DOCUMENTS

| | | |
|---|---|---|
| 6,169,190 B1 | 1/2001 | Lanuza et al. |
| 6,215,042 B1 | 4/2001 | Willmitzer et al. |
| 6,229,072 B1 | 5/2001 | Burns et al. |
| 6,270,828 B1 | 8/2001 | DeBonte et al. |
| 6,284,479 B1 | 9/2001 | Nichols |
| 6,323,392 B1 | 11/2001 | Charne |
| 6,734,341 B2 | 5/2004 | Singletary et al. |
| 6,893,650 B1 | 5/2005 | Charles et al. |
| 7,112,665 B1 | 9/2006 | Leemans et al. |
| 2002/0031826 A1 | 3/2002 | Nichols |
| 2003/0176428 A1 | 9/2003 | Schneidersmann et al. |
| 2004/0241098 A1 | 12/2004 | Labourdette et al. |
| 2004/0266867 A1 | 12/2004 | Cheng et al. |
| 2005/0182025 A1 | 8/2005 | Tseng |
| 2006/0052459 A1 | 3/2006 | Vors et al. |
| 2009/0018176 A1 | 1/2009 | Dahmen et al. |

FOREIGN PATENT DOCUMENTS

| | | |
|---|---|---|
| EP | 0 719 338 A1 | 7/1996 |
| EP | 0 837 994 A2 | 4/1998 |
| EP | 0 728 213 B1 | 1/2004 |
| EP | 0 663 956 B1 | 6/2005 |
| JP | 2006-304779 A | 11/2006 |
| WO | 89/10396 A1 | 11/1989 |
| WO | 91/02069 A1 | 2/1991 |
| WO | 92/05251 A1 | 4/1992 |
| WO | 94/04693 A2 | 3/1994 |
| WO | 94/09144 A1 | 4/1994 |
| WO | 94/11520 A2 | 5/1994 |
| WO | 94/21795 A1 | 9/1994 |
| WO | 95/04826 A1 | 2/1995 |
| WO | 95/09910 A1 | 4/1995 |
| WO | 95/26407 A1 | 10/1995 |
| WO | 95/31553 A1 | 11/1995 |
| WO | 95/35026 A1 | 12/1995 |
| WO | 96/01904 A1 | 1/1996 |
| WO | 96/15248 A1 | 5/1996 |
| WO | 96/19581 A1 | 5/1996 |
| WO | 96/21023 A1 | 7/1996 |
| WO | 96/27674 A1 | 9/1996 |
| WO | 96/33270 A1 | 10/1996 |
| WO | 96/34968 A2 | 11/1996 |
| WO | 96/38567 A2 | 12/1996 |
| WO | 97/11188 A1 | 3/1997 |
| WO | 97/20936 A1 | 6/1997 |
| WO | 97/26362 A1 | 7/1997 |
| WO | 97/32985 A1 | 9/1997 |
| WO | 97/41218 A1 | 11/1997 |
| WO | 97/42328 A1 | 11/1997 |
| WO | 97/44472 A1 | 11/1997 |
| WO | 97/45545 A1 | 12/1997 |
| WO | 97/47806 A1 | 12/1997 |
| WO | 97/47807 A1 | 12/1997 |
| WO | 97/47808 A1 | 12/1997 |
| WO | 98/00549 A1 | 1/1998 |
| WO | 98/20145 A2 | 5/1998 |
| WO | 98/22604 A1 | 5/1998 |
| WO | 98/27212 A1 | 6/1998 |
| WO | 98/27806 A1 | 7/1998 |
| WO | 98/32326 A2 | 7/1998 |
| WO | 98/39460 A1 | 9/1998 |
| WO | 98/40503 A1 | 9/1998 |
| WO | 99/12950 A2 | 3/1999 |
| WO | 99/24585 A1 | 5/1999 |
| WO | 99/24586 A1 | 5/1999 |
| WO | 99/24593 A1 | 5/1999 |
| WO | 99/34008 A1 | 7/1999 |
| WO | 99/53072 A1 | 10/1999 |
| WO | 99/57965 A1 | 11/1999 |
| WO | 99/58654 A2 | 11/1999 |
| WO | 99/58688 A2 | 11/1999 |
| WO | 99/58690 A2 | 11/1999 |
| WO | 99/66050 A1 | 12/1999 |
| WO | 00/04173 A1 | 1/2000 |
| WO | 00/08184 A1 | 2/2000 |
| WO | 00/08185 A1 | 2/2000 |
| WO | 00/11192 A2 | 3/2000 |
| WO | 00/14249 A1 | 3/2000 |
| WO | 00/22140 A1 | 4/2000 |
| WO | 00/28052 A2 | 5/2000 |
| WO | 00/47727 A2 | 8/2000 |
| WO | 00/66746 A1 | 11/2000 |
| WO | 00/66747 A1 | 11/2000 |
| WO | 00/73422 A1 | 12/2000 |
| WO | 00/77229 A2 | 12/2000 |
| WO | 01/12782 A2 | 2/2001 |
| WO | 01/12826 A2 | 2/2001 |
| WO | 01/14569 A2 | 3/2001 |
| WO | 01/17333 A1 | 3/2001 |
| WO | 01/19975 A2 | 3/2001 |
| WO | 01/24615 A1 | 4/2001 |
| WO | 01/65922 A2 | 9/2001 |
| WO | 01/66704 A2 | 9/2001 |
| WO | 01/98509 A2 | 12/2001 |
| WO | 02/26995 A1 | 4/2002 |
| WO | 02/28186 A2 | 4/2002 |
| WO | 02/34923 A2 | 5/2002 |
| WO | 02/36782 A2 | 5/2002 |
| WO | 02/45485 A1 | 6/2002 |
| WO | 02/079410 A2 | 10/2002 |
| WO | 02/080675 A1 | 10/2002 |
| WO | 02/101059 A2 | 12/2002 |
| WO | 03/013226 A1 | 2/2003 |
| WO | 03/033540 A2 | 4/2003 |
| WO | 03/071860 A2 | 9/2003 |
| WO | 03/092360 A2 | 11/2003 |
| WO | 2004/024928 A2 | 3/2004 |
| WO | 2004/040012 A2 | 5/2004 |
| WO | 2004/053219 A2 | 6/2004 |
| WO | WO 2004046118 A2 * | 6/2004 |
| WO | 2004/056999 A1 | 7/2004 |
| WO | 2004/007893 A2 | 9/2004 |
| WO | 2004/090140 A2 | 10/2004 |
| WO | 2004/106529 A2 | 12/2004 |
| WO | 2005/002324 A2 | 1/2005 |
| WO | 2005/002359 A2 | 1/2005 |
| WO | 2005/012515 A2 | 2/2005 |
| WO | 2005/017157 A1 | 2/2005 |
| WO | 2005/020673 A1 | 3/2005 |
| WO | 2005/030941 A1 | 4/2005 |
| WO | 2005/030942 A1 | 4/2005 |
| WO | 2005/089547 A1 | 9/2005 |
| WO | 2005089547 | 9/2005 |
| WO | 2005/012529 A1 | 10/2005 |
| WO | 2005/093093 A2 | 10/2005 |
| WO | 2005/095617 A2 | 10/2005 |
| WO | 2005/095618 A2 | 10/2005 |
| WO | 2005/095619 A1 | 10/2005 |
| WO | 2005/095632 A2 | 10/2005 |
| WO | 2005/120234 A2 | 12/2005 |
| WO | 2005/123927 A1 | 12/2005 |
| WO | 2005120234 | 12/2005 |
| WO | 2006/007373 A2 | 1/2006 |
| WO | 2006/015376 A2 | 2/2006 |
| WO | 2006/018319 A1 | 2/2006 |
| WO | 2006/021972 A1 | 3/2006 |
| WO | 2006/024351 A1 | 3/2006 |
| WO | 2006/032469 A2 | 3/2006 |
| WO | 2006/032538 A1 | 3/2006 |
| WO | 2006/045633 A1 | 5/2006 |
| WO | 2006/060634 A2 | 6/2006 |
| WO | 2006/063862 A1 | 6/2006 |
| WO | 2006/072603 A2 | 7/2006 |
| WO | 2006/103107 A1 | 10/2006 |
| WO | 2006/108702 A1 | 10/2006 |
| WO | 2006/133827 A2 | 12/2006 |
| WO | 2006/136351 A2 | 12/2006 |
| WO | 2007/009823 A1 | 1/2007 |
| WO | 2007/024782 A2 | 3/2007 |
| WO | 2007/027777 A2 | 3/2007 |
| WO | 2007/039314 A2 | 4/2007 |
| WO | 2007/039315 A1 | 4/2007 |
| WO | 2007/039316 A1 | 4/2007 |
| WO | 2007/107326 A1 | 9/2007 |
| WO | 2007/131699 A2 | 11/2007 |
| WO | 2008/017518 A1 | 2/2008 |

| | | |
|---|---|---|
| WO | 2008/080630 A1 | 7/2008 |
| WO | 2008/080631 A1 | 7/2008 |
| WO | 2008/090008 A1 | 7/2008 |

OTHER PUBLICATIONS

Gasser et al., "Structure, Expression, and Evolution of the 5-Enolpyruvylshikimate-3-phosphate Synthase Genes of *Petunia* and Tomato," Journal of Biological Chemistry, vol. 263, No. 9, Mar. 25, 1988, pp. 4280-4289.

Tranel et al., "Resistance of weeds to ALS-inhibiting herbicides: what have we learned?" Weed Science, 2002, 50, pp. 700-712.

Crickmore et al., "Revision of the Nomenclature for the *Bacillus thuringiensis* Pesticidal Crystal Proteins," Microbiology and Molecular Biology Reviews, Sep. 1998, vol. 62, No. 3, pp. 807-813.

Moellenbeck et al., "Insecticidal proteins from *Bacillus thuringiensis* protect corn from corn rootworms," Nature Biotechnology, vol. 19, Jul. 2001, pp. 668-672.

Schnepf et al., "Characterization of Cry34/Cry35 Binary Insecticidal Proteins from Diverse *Bacillus thuringiensis* Strain Collections," Applied and Environmental Microbiology, Apr. 2005, vol. 71, No. 4, pp. 1765-1774.

\* cited by examiner

SUBSTITUTED PHENYLAMIDINES AND THE USE THEREOF AS FUNGICIDES

CROSS REFERENCE TO RELATED APPLICATIONS

This application is a §371 National Stage Application of PCT/EP2008/001861 filed Mar. 8, 2008, which claims priority to European Application 07004998.6 filed Mar. 12, 2007.

BACKGROUND OF THE INVENTION

1. Field of the Invention

The present invention relates to oxime ether-, hydrazone- or azomethine-substituted phenylamidines of the general formula (I), to a process for their preparation, to the use of the amidines according to the invention for controlling unwanted microorganisms and also to a composition for this purpose, comprising the amidines according to the invention. Furthermore, the invention relates to a method for controlling unwanted microorganisms by applying the compounds according to the invention to the microorganisms and/or their habitat.

2. Description of Related Art

WO-A-00/046 184 discloses the use of amidines as fungicides.

WO-A-03/093 224 discloses the use of arylamidine derivatives, in particular of N-ethyl-N-methyl-N'-[4-(3-trimethylsilylpropyl-1-oxy)-2,5-dimethylphenyl]formamidine, as fungicides.

WO-A-03/024 219 discloses fungicide compositions comprising at least one N2-phenylamidine derivative in combination with a further selected known active compound.

WO-A-04/037239 discloses antifungicidal medicaments based on N2-phenylamidine derivatives.

WO-A-05/089 547 discloses fungicide mixtures comprising at least one arylamidine derivative in combination with a further known fungicidally active compound.

WO-A-05/120 234 discloses fungicide mixtures comprising at least one phenylamidine derivative and a further selected known fungicide.

The effectiveness of the amidines described in the prior art is good but in many cases leaves something to be desired.

SUMMARY OF THE INVENTION

Accordingly, it is the object of the present invention to provide amidines having an improved fungicidal effectiveness.

Surprisingly, this object has been achieved by substituted phenylamidines of the formula (I)

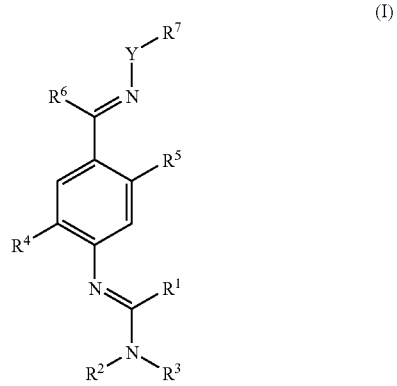

(I)

in which

Y is selected from the group consisting of O, NH and a single bond;

$R^1$ is selected from the group consisting of hydrogen; straight-chain or branched $C_{1-12}$-alkyl, $C_{2-12}$-alkenyl, $C_{2-12}$-alkynyl groups, cyclic $C_{3-8}$-alkyl, $C_{4-8}$-alkenyl and $C_{4-8}$-alkynyl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' may represent hydrogen or a $C_{1-12}$-alkyl group;

—SH; —SR", where R" may represent a straight-chain or branched $C_{1-12}$-alkyl group which may be substituted by one or more groups selected from the group consisting of —R', —X, —OR', —SR', —NR'$_2$, —SiR'$_3$, —COOR', —CN and —CONR'$_2$, where R' has the above meanings;

$R^2$ is selected from the group consisting of straight-chain or branched $C_{1-12}$-alkyl, $C_{2-12}$-alkenyl, $C_{2-12}$-alkynyl groups, cyclic $C_{3-8}$-alkyl, $C_{4-8}$-alkenyl or $C_{4-8}$-alkynyl groups, $C_{5-18}$-aryl, $C_{7-19}$-aralkyl and $C_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' has the above meanings;

$R^3$ is selected from the group consisting of —CN, —SH, —SR", —OR", —(C=O)—R", straight-chain or branched $C_{1-12}$-alkyl, $C_{2-12}$-alkenyl, $C_{2-12}$-alkynyl groups, cyclic $C_{3-8}$-alkyl, $C_{4-8}$-alkenyl and $C_{4-8}$-alkynyl groups, $C_{5-18}$-aryl, $C_{7-19}$-aralkyl and $C_{7-19}$-alkaryl groups, where in and the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' and R" have the above meanings;

or in which $R^2$ and $R^3$, $R^2$ and $R^1$ or $R^1$ and $R^3$ together with the atoms to which they are attached or together with further atoms selected from the group consisting of N, O, P and S may form a four- to seven-membered ring which for its part may be substituted by one or more X, R', OR', SR', NR'$_2$, SiR'$_3$, COOR', CN and CONR'$_2$ groups, where R' has the above meanings;

$R^4$ is selected from the group consisting of —X, —CN, —SH, —SR", —OR", —(C=O)—R", straight-chain or branched $C_{1-12}$-alkyl, $C_{2-12}$-alkenyl, $C_{2-12}$-alkynyl groups, cyclic $C_{3-8}$-alkyl, $C_{4-8}$-alkenyl and $C_{4-8}$-alkynyl groups, $C_{5-18}$-aryl, $C_{7-19}$-aralkyl and $C_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' and R" have the above meanings;

$R^5$ is selected from the group consisting of hydrogen, —X, —CN, —SH, —SR", —OR", —(C=O)—R", straight-chain or branched $C_{1-12}$-alkyl, $C_{2-12}$-alkenyl, $C_{2-12}$-alkynyl groups, cyclic $C_{3-8}$-alkyl, $C_{4-8}$-alkenyl and $C_{4-8}$-alkynyl groups, $C_{5-18}$-aryl, $C_{7-19}$-aralkyl and $C_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' and R" have the above meanings;

$R^6$ is selected from the group consisting of hydrogen; straight-chain or branched $C_{1-12}$-alkyl, $C_{2-12}$-alkenyl, $C_{2-12}$-alkynyl groups, cyclic $C_{3-8}$-alkyl, $C_{4-8}$-alkenyl and $C_{4-8}$-alkynyl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, —SH; —SR", where R' and R" have the above meanings;

$R^7$ is selected from groups (i) to (iii) below:
(i) $C_{5-18}$-aryl or $C_{7-19}$-alkaryl groups of the formula (II) in whose ring system one, two or more carbon atoms may be replaced by heteroatoms selected from the group consisting of N, O, P, S,

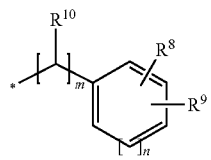

(II)

in which
m represents 0, 1, 2 or 3
n represents 0 or 1,
$R^8$ is selected from the group consisting of hydrogen, —X, —CN, —SH, —SR", —OR", —(C=O)—R"; straight-chain or branched $C_{1-12}$-alkyl, $C_{2-12}$-alkenyl, $C_{2-12}$-alkynyl groups, cyclic $C_{3-8}$-alkyl, $C_{4-8}$-alkenyl and $C_{4-8}$-alkynyl groups and $C_{5-18}$-aryl, $C_{7-19}$-aralkyl and $C_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' and R" have the above meanings;

$R^9$ is selected from the group consisting of hydrogen, —X, —CN, —SH, —SR", —OR", —(C=O)—R"; straight-chain or branched $C_{1-12}$-alkyl, $C_{2-12}$-alkenyl, $C_{2-12}$-alkynyl groups, $C_{3-8}$-alkyl, $C_{4-8}$-alkenyl and $C_{4-8}$-alkynyl groups and $C_{5-18}$-aryl, $C_{7-19}$-aralkyl and $C_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' and R" have the above meanings;

or in which $R^8$ and $R^9$ together with the skeleton atoms to which they are attached or with one, two or more atoms selected from the group consisting of N, O, P and S may form a four- to seven-membered ring which may be substituted by one or more X, R', OR', SR', NR'$_2$, SiR'$_3$, COOR', CN— and CONR'$_2$ groups, where R' hydrogen, has the above meanings;

$R^{10}$ is selected from the group consisting of hydrogen and straight-chain and branched $C_{1-12}$-alkyl groups and cyclic $C_{3-12}$-alkyl groups where in the ring system of the cyclic groups mentioned above one or more carbon atoms may be replaced by heteroatoms selected from the group consisting of N, O, P and S;

(ii) straight-chain or branched $C_{1-12}$-alkyl, $C_{2-12}$-alkenyl, $C_{2-12}$-alkynyl groups, cyclic $C_{3-8}$-alkyl, $C_{4-8}$-alkenyl and $C_{4-8}$-alkynyl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' has the above meanings;

(iii) radicals of the formula (III)

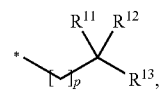

(III)

in which
p represents 0, 1, 2 or 3,
$R^{11}$ to $R^{13}$ independently of one another are selected from the group consisting of hydrogen, straight-chain or branched $C_{1-12}$-alkyl, $C_{2-12}$-alkenyl, $C_{2-12}$-alkynyl groups, cyclic $C_{3-8}$-alkyl, $C_{4-8}$-alkenyl and $C_{4-8}$-alkynyl groups and $C_{5-18}$-aryl, $C_{7-19}$-aralkyl and $C_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' has the above meanings;

and their salts.

The present invention furthermore provides a process for preparing the substituted phenylamidines as claimed in any of claims 1 to 4 which comprises at least one of the following steps (a) to (f):

(a) reaction of nitrobenzaldehydes or nitrobenzoketones of the formula (IV) with amines of the formula (V) according to the reaction scheme below:

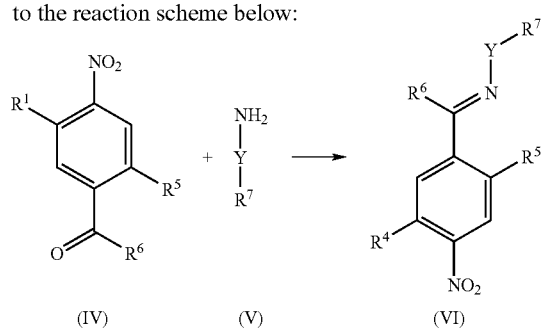

(b) reaction of aminobenzaldehydes or aminobenzoketones of the formula (VII) with amines of the formula (V) according to the reaction scheme below:

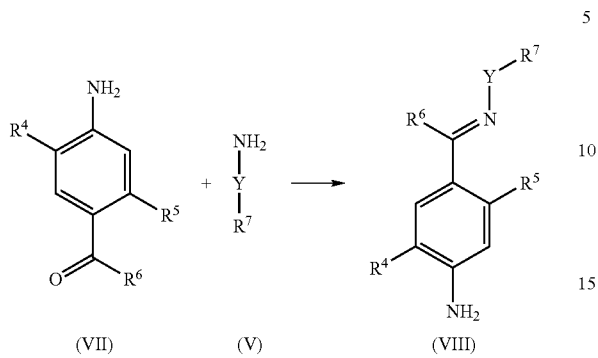

(c) reduction of the nitroaromatics of the formula (VI) to anilines of the formula (VIII) according to the reaction scheme below:

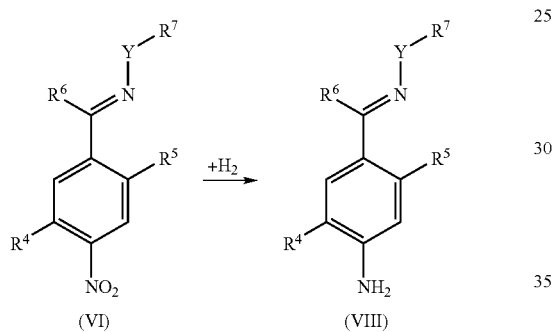

(d) reaction of the anilinoxime ethers of the formula (VIII) with
(i) aminoacetals of the formula (XIII) or
(ii) with amides of the formula (XIV) or
(iii) with amines of the formula (XV) in the presence of ortho esters of the formula (XVI) according to the reaction scheme below:

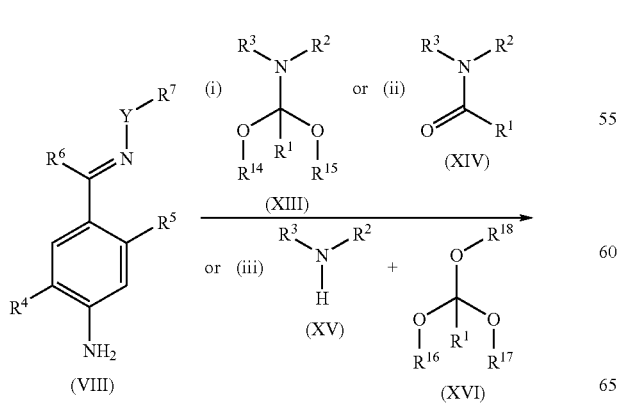

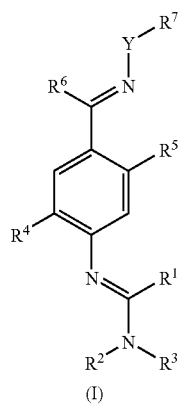

(e) reaction of the aminobenzaldehydes or aminobenzoketones of the formula (VII) with
(i) aminoacetals of the formula (XIII) or
(ii) with amides of the formula (XIV) or
(iii) with amines of the formula (XV) in the presence of ortho esters of the formula (XVI) according to the reaction scheme below:

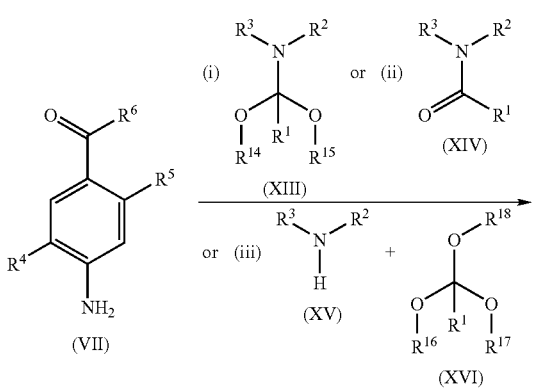

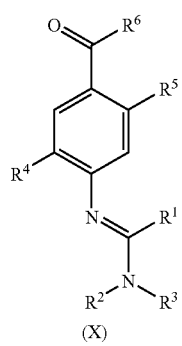

(f) reaction of amidines of the formula (X) with amines of the formula (V) according to the reaction scheme below:

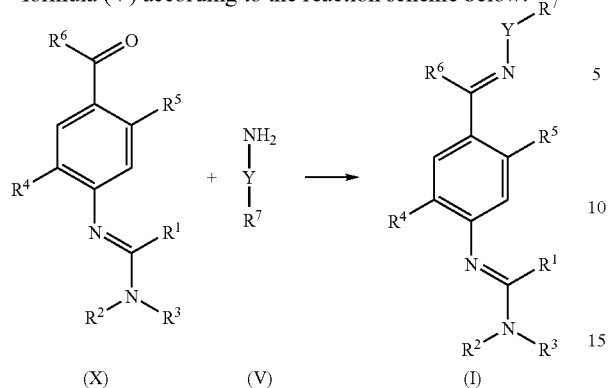

(X)    (V)    (I)

where in the above schemes
Y, $R^1$ to $R^{13}$ have the above meanings;
$R^{14}$ and $R^{15}$ independently of one another are selected from the group consisting of hydrogen, $C_{1-12}$-alkyl, $C_{2-12}$-alkenyl, $C_{2-12}$-alkynyl or $C_{5-18}$-aryl or $C_{7-19}$-arylalkyl groups and together with the oxygen atoms to which they are attached may form a five-, six- or seven-membered ring;
$R^{16}$, $R^{17}$ and $R^{18}$ independently of one another are selected from the group consisting of hydrogen, $C_{1-12}$-alkyl, $C_{2-12}$-alkenyl, $C_{2-12}$-alkynyl or $C_{5-18}$-aryl or $C_{7-19}$-arylalkyl, $C_{7-19}$-alkylaryl groups and in each case $R^{10}$ with $R^{12}$, $R^{10}$ with $R^{11}$ or $R^{11}$ with $R^{12}$ together with the oxygen atoms to which they are attached may form a five-, six- or seven-membered ring.

A third subject matter of the invention relates to amidines of the formula (X)

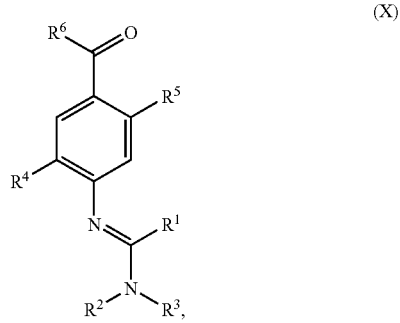

(X)

in which
$R^1$ to $R^6$ have the above meanings.

A fourth subject matter of the invention relates to nitrobenzaldehydes of the formula (IV)

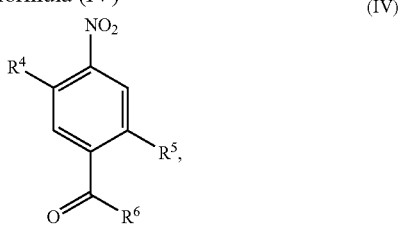

(IV)

in which
$R^1$ to $R^6$ have the above meanings.

A fifth subject matter of the invention relates to aminobenzaldehydes or aminobenzoketones of the formula (VII)

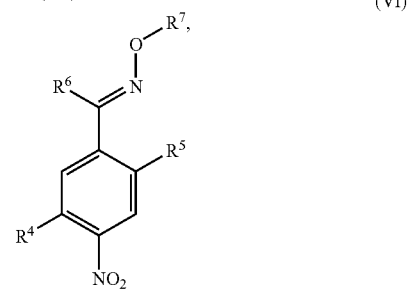

(VII)

in which
$R^1$ to $R^6$ have the above meanings.

A sixth subject matter of the invention relates to nitrooxime ethers of the formula (VI)

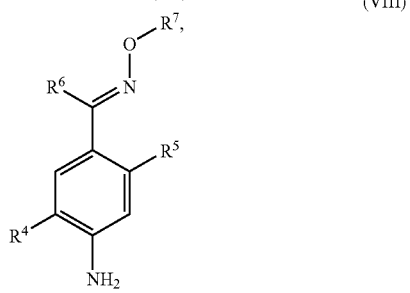

(VI)

in which
$R^4$ to $R^7$ have the above meanings.

A seventh subject matter of the invention relates to nitrooxime ethers of the formula (VI)

(VIII)

in which
$R^4$ to $R^7$ have the above meanings.

An eighth subject matter of the invention is the use of the substituted phenylamidines according to the invention or of mixtures of these for controlling unwanted microorganisms.

A ninth subject matter of the present invention is a composition for controlling unwanted microorganisms, comprising at least one substituted phenylamidine according to the present invention.

A further subject matter of the invention relates to a method for controlling unwanted microorganisms, characterized in that the amidines according to the invention are applied to the microorganisms and/or their habitat.

Moreover, the invention relates to seed which has been treated with at least one of the amidines according to the invention.

A final subject matter of the invention relates to a method for protecting seed against unwanted microorganisms by using seed treated with at least one phenoxyamidine of the present invention.

DETAILED DESCRIPTION OF A PREFERRED EMBODIMENT

In connection with the present invention, the term halogens (X) comprises, unless otherwise defined, those elements which are chosen from the group consisting of fluorine, chlorine, bromine and iodine, where fluorine, chlorine and bromine are preferably used and fluorine and chlorine are particularly preferably used.

Optionally substituted groups can be mono- or polysubstituted, where in the case of polysubstitution the substituents can be identical or different.

In connection with the present invention, the group —X denotes a halogen atom selected from the group consisting of fluorine, chlorine, bromine and iodine, preferably fluorine, chlorine and bromine, particularly preferably from the group consisting of fluorine and chlorine.

Alkyl groups substituted by one or more halogen atoms (—X) are, for example, selected from the group consisting of trifluoromethyl ($CF_3$), difluoromethyl ($CHF_2$), $CF_3CH_2$, $ClCH_2$, $CF_3CCl_2$.

In connection with the present invention, alkyl groups are, unless otherwise defined, straight-chain, branched or cyclic hydrocarbon groups which may optionally have one, two or more single or double unsaturations or one, two or more heteroatoms selected from the group consisting of O, N, P and S. Moreover, the alkyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR'$_2$), where R' represents hydrogen or a $C_{1-12}$-alkyl group, preferably a $C_{2-10}$-alkyl group, particularly preferably a $C_{3-8}$-alkyl group which may have one or more heteroatoms selected from the group consisting of N, O, P and S.

The definition $C_1$-$C_{12}$-alkyl comprises the biggest range defined herein for an alkyl group. Specifically, this definition comprises, for example, the meanings methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In connection with the present invention, alkenyl groups are, unless otherwise defined, straight-chain, branched or cyclic hydrocarbon groups which comprise at least one single unsaturation (double bond) and may optionally have one, two or more single or double unsaturations or one, two or more heteroatoms selected from the group consisting of O, N, P and S. Moreover, the alkenyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR'$_2$), where R' represents hydrogen or a $C_{1-12}$-alkyl group, preferably $C_{2-10}$-alkyl group, particularly preferably $C_{3-8}$-alkyl group, which may have one or more heteroatoms selected from the group consisting of N, O, P and S.

The definition $C_2$-$C_{12}$-alkenyl comprises the biggest range defined herein for an alkenyl group. Specifically, this definition comprises, for example, the meanings vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-1'-enyl; buta-1,3-dienyl, penta-1,3-dienyl.

In connection with the present invention, alkynyl groups are, unless otherwise defined, straight-chain, branched or cyclic hydrocarbon groups which comprise at least one double unsaturation (triple bond) and may optionally have one, two or more single or double unsaturations or one, two or more heteroatoms selected from the group consisting of O, N, P and S. Moreover, the alkynyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl-(—(C=O)R') and amide groups (—CONR'$_2$), where R' represents hydrogen or a straight-chain, branched or cyclic $C_{1-12}$-alkyl group which may have one or more heteroatoms selected from the group consisting of N, O, P and S.

The definition $C_2$-$C_{12}$-alkynyl comprises the biggest range defined herein for an alkynyl group. Specifically, this definition comprises, for example, the meanings ethynyl (acetylenyl), prop-1-ynyl and prop-2-ynyl.

In connection with the present invention, aryl groups are, unless otherwise defined, aromatic hydrocarbon groups which may have one, two or more heteroatoms selected from the group consisting of O, N, P and S and may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR'$_2$), where R' represents hydrogen or a $C_{1-12}$-alkyl group, preferably $C_{2-10}$-alkyl group, particularly preferably $C_{3-8}$-alkyl group, which may have one or more heteroatoms selected from the group consisting of N, O, P and S.

The definition $C_{5-18}$-aryl comprises the biggest range defined herein for an aryl group having 5 to 18 atoms. Specifically, this definition comprises, for example, the meanings cyclopentadienyl, phenyl, cyclo-heptatrienyl, cyclooctatetraenyl, naphthyl and anthracenyl.

In connection with the present invention, arylalkyl groups (aralkyl groups) are, unless otherwise defined, alkyl groups substituted by aryl groups which may have a $C_{1-8}$-alkylene chain and may be substituted in the aryl skeleton or in the alkylene chain by one or more heteroatoms selected from the group consisting of O, N, P and S and optionally by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR'$_2$), where R' represents hydrogen or a $C_{1-12}$-alkyl group, preferably $C_{2-10}$-alkyl group, particularly preferably $C_{3-8}$-alkyl group, which may have one or more heteroatoms selected from the group consisting of N, O, P and S.

The definition $C_{7-19}$-aralkyl group comprises the biggest range defined herein for an aralkyl group having a total of 7 to 19 atoms in the skeleton and the alkylene chain. Specifically, this definition comprises, for example, the meanings benzyl and phenylethyl.

In connection with the present invention, alkylaryl groups (alkaryl groups) are, unless otherwise defined, aryl groups substituted by alkyl groups which may have a $C_{1-8}$-alkylene chain and may be substituted in the aryl skeleton or the alkylene chain by one or more heteroatoms selected from the group consisting of O, N, P and S and optionally by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR'$_2$), where R' represents hydrogen or a C$_{1-12}$-alkyl group, preferably C$_{2-10}$-alkyl group, particularly preferably C$_{3-8}$-alkyl group, which may have one or more heteroatoms selected from the group consisting of N, O, P and S.

The definition C$_{7-19}$-alkylaryl group comprises the biggest range defined herein for an alkylaryl group having a total of 7 to 19 atoms in the skeleton and the alkylene chain. Specifically, this definition comprises, for example, the meanings tolyl, 2,3-, 2,4-, 2,5-, 2,6-, 3,4- or 3,5-dimethylphenyl.

The alkyl, alkenyl, alkynyl, aryl, alkaryl and aralkyl groups may furthermore have one or more heteroatoms which—unless otherwise defined—are chosen from the group consisting of N, O, P and S. Here, the heteroatoms replace the carbon atoms indicated.

Not included are combinations which are contrary to natural laws and which the person skilled in the art, based on his expert knowledge, would thus have excluded. Excluded are, for example, ring structures having three or more adjacent oxygen atoms.

The compounds according to the invention may, if appropriate, exist as mixtures of different possible isomeric forms, in particular stereoisomers, such as, for example, E- and Z-, threo- and erythro-, and also optical isomers, but, if appropriate, also tautomers. What is disclosed and claimed are both the E- and the Z-isomers, and also the threo- and erythro-, and also the optical isomers, any mixtures of these isomers, and also the possible tautomeric forms.

The substituted phenylamidines according to the invention are compounds of the formula (I)

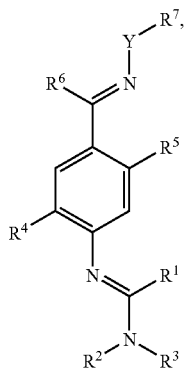

(I)

or their salts, N-oxides, metal complexes and their stereoisomers.

In the formula (I), the groups have the meanings defined below. The given definitions also apply to all intermediates:
Y is selected from the group consisting of O, NH and a.
R$^1$ is selected from the group consisting of:
  hydrogen;
  straight-chain or branched C$_{1-12}$-alkyl, C$_{2-12}$-alkenyl, C$_{2-12}$-alkynyl groups;
  cyclic C$_{3-8}$-alkyl, C$_{4-8}$-alkenyl or C$_{4-8}$-alkynyl groups;
where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide groups (—CONR'$_2$), where R' may represent hydrogen or a C$_{1-12}$-alkyl group, preferably C$_{2-10}$-alkyl group, particularly preferably C$_{3-8}$-alkyl group;

mercapto (—SH) and thioether groups (—SR''), where R'' may represent a straight-chain or branched C$_{1-12}$-alkyl group, preferably C$_{2-10}$-alkyl group, particularly preferably C$_{3-8}$-alkyl group, which may be substituted by groups, where the groups mentioned above are selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide groups (—CONR'$_2$), where R$^1$ has the above meanings.
R$^2$ is selected from the group consisting of:
  straight-chain or branched C$_{1-12}$-alkyl, C$_{2-12}$-alkenyl, C$_{2-12}$-alkynyl groups;
  cyclic C$_{3-12}$-alkyl, C$_{4-12}$-alkenyl, C$_{4-12}$-alkynyl groups;
  C$_{5-18}$-aryl, C$_{7-19}$-aralkyl or C$_{7-19}$-alkaryl groups,
where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide groups (—CONR'$_2$), where R' has the above meanings.
R$^3$ is selected from the group consisting of:
  cyano (—CN), mercapto (—SH), thioether (—SR''), alkoxy (—OR'') and acyl groups (—(C=O)—R''), where R' has the above meanings;
  straight-chain or branched C$_{1-12}$-alkyl, C$_{2-12}$-alkenyl, C$_{2-12}$-alkynyl groups, cyclic C$_{3-12}$-alkyl, C$_{4-12}$-alkenyl, C$_{4-12}$-alkynyl groups, C$_{5-18}$-aryl, C$_{7-19}$-aralkyl or C$_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide groups (—CONR'$_2$), where R' has the above meanings.

In an alternative embodiment of the present invention, R$^2$ and R$^3$, R$^2$ and R$^1$ or R$^1$ and R$^3$ together with the atoms to which they are attached or with further atoms selected from the group consisting of N, O, P and S may form a four- to seven-membered ring which for its part may be substituted by one or more R', halogen (—X), alkoxy (—OR'), thioether or mercapto (—SR'), amino (—NR'$_2$), silyl (—SiR'$_3$), carboxyl (—COOR'), cyano (—CN) and amide groups (—CONR'$_2$) where R' has the above meanings;
R$^4$ is selected from the group consisting of:
  halogen atoms (X—);
  cyano (—CN), mercapto (—SH), thioether (—SR''), alkoxy (—OR'') and acyl groups (—(C=O)—R''), where R'' has the above meanings;
  straight-chain or branched C$_{1-12}$-alkyl, C$_{2-12}$-alkenyl, C$_{2-12}$-alkynyl groups, cyclic C$_{3-12}$-alkyl, C$_{4-12}$-alkenyl, C$_{4-12}$-alkynyl groups, C$_{5-18}$-aryl, C$_{7-19}$-aralkyl or C$_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide groups (—CONR'$_2$), where R' has the above meanings.

R$^5$ is selected from the group consisting of:
  hydrogen;
  halogen atoms (X—), cyano (—CN), mercapto (—SH), thioether (—SR"), alkoxy (—OR") and acyl groups (—(C=O)—R"), where R" has the above meanings;
  straight-chain or branched C$_{1-12}$-alkyl, C$_{2-12}$-alkenyl, C$_{2-12}$-alkynyl groups, cyclic C$_{3-8}$-alkyl, C$_{4-8}$-alkenyl, C$_{4-8}$-alkynyl groups C$_{5-18}$-aryl, C$_{7-19}$-aralkyl or C$_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide groups (—CONR'$_2$), where R' has the above meanings.

R$^6$ is selected from the group consisting of:
  hydrogen;
  straight-chain or branched C$_{1-12}$-alkyl, C$_{2-12}$-alkenyl, C$_{2-12}$-alkynyl groups, cyclic C$_{3-8}$-alkyl, C$_{4-8}$-alkenyl, C$_{4-8}$-alkynyl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN) and amide groups (—CONR'$_2$);
  thioether (—SR") or mercapto groups (—SH),
where R' and R" have the above meanings.

R$^7$ is selected from groups (i) to (iii) below:
  (i) C$_{5-18}$-aryl or C$_{7-19}$-alkaryl groups of the formula (II) in whose ring system one, two or more carbon atoms may be replaced by heteroatoms selected from the group consisting of N, O, P, S

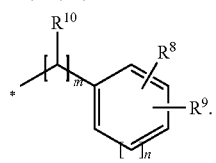
(II)

The radicals in the formula (II) have the following meanings:
* denotes the bond to the Y atom.
m is an integer selected from the group consisting of 0, 1, 2 and 3.
n is an integer selected from the group consisting of 0 and 1. If m=0, the group of the formula (II) is an aryl or heteroaryl group, if m=1, 2 or 3 an alkaryl or heteroalkaryl group.

R$^8$ is selected from the group consisting of
  hydrogen;
  —X, —CN, —SH, —SR", —OR", —(C=O)—R",
  straight-chain or branched C$_{1-12}$-alkyl, C$_{2-12}$-alkenyl, C$_{2-12}$-alkynyl groups, cyclic C$_{3-12}$-alkyl, C$_{4-12}$-alkenyl, C$_{4-12}$-alkynyl groups or C$_{5-18}$-aryl, C$_{7-19}$-aralkyl or C$_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$,
where R' and R" have the above meanings.

R$^9$ is selected from the group consisting of
  hydrogen,
  —X, —CN, —SH, —SR", —OR", —(C=O)—R",
  straight-chain or branched C$_{1-12}$-alkyl, C$_{2-12}$-alkenyl, C$_{2-12}$-alkynyl groups, cyclic C$_{3-8}$-alkyl, C$_{4-8}$-alkenyl, C$_{4-8}$-alkynyl groups or C$_{5-18}$-aryl, C$_{7-19}$-aralkyl or C$_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$,
where R' and R" have the above meanings.

Alternatively, R$^8$ and R$^9$ together with the skeleton atoms to which they are attached or with one, two or more atoms selected from the group consisting of N, O, P and S may form a four- to seven-membered ring which may be substituted by one or more X, R', OR', SR', NR'$_2$—, SiR'$_3$, COOR', CN and CONR'$_2$ groups, where R' has the above meanings.

R$^{10}$ is selected from the group consisting of
  hydrogen,
  straight-chain or branched C$_{1-12}$-alkyl, C$_{2-12}$-alkenyl, C$_{2-12}$-alkynyl groups or cyclic C$_{3-12}$-alkyl groups, where in the ring system of the cyclic groups mentioned above one or more carbon atoms may be replaced by heteroatoms selected from the group consisting of N, O, P and S and
where R' has the above meanings.

(ii) In an alternative embodiment according to the invention, the group R$^7$ is selected from the group consisting of straight-chain or branched C$_{1-12}$-alkyl, C$_{2-12}$-alkenyl, C$_{2-12}$-alkynyl groups, cyclic C$_{3-8}$-alkyl, C$_{4-8}$-alkenyl, C$_{4-8}$-alkynyl groups, where in the ring system of all of the cyclic groups mentioned above one or more carbon atoms may be replaced by heteroatoms selected from the group consisting of N, O, P and S and where all of the groups mentioned above may be substituted by one or more groups selected from the group consisting of —R', —X, —OR', —SR', —NR'$_2$, —SiR'$_3$, —COOR', —CN and —CONR'$_2$, where R' has the above meanings.

(iii) In a further alternative embodiment, the group R$^7$ is selected from among radicals of the formula (III).

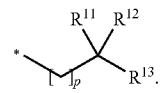
(III)

In formula (III), the radicals have the following meanings:
* denotes the bond to the Y atom.
p represents an integer selected from the group consisting of 0, 1, 2 and 3.
R$^{11}$ to R$^{13}$ independently of one another are selected from the group consisting of
  hydrogen,
  straight-chain or branched C$_{1-12}$-alkyl, C$_{2-12}$-alkenyl, C$_{2-12}$-alkynyl groups, cyclic C$_{3-8}$-alkyl, C$_{4-8}$-alkenyl, C$_{4-8}$-alkynyl groups or C$_{5-18}$-aryl, C$_{7-19}$-aralkyl or C$_{7-19}$-alkaryl groups, where in the ring system of all of the cyclic groups mentioned above one or more carbon atoms may be replaced by heteroatoms selected from the group consisting of N, O, P and S and all of the groups mentioned above may be substituted by one or more groups selected from the group consisting of —R', —X, —OR', —SR', —NR'$_2$, —SiR'$_3$, —COOR', —CN and —CONR'$_2$, where R' has the above meanings.

In formula (I), the radicals have the preferred meanings defined below. The definitions given as being preferred likewise apply to all intermediates:

Y is preferably selected from the group consisting of 0 and a single bond.

$R^1$ is preferably selected from the group consisting of hydrogen, a mercapto group (—SH) or $C_{1-8}$-alkyl group.

$R^2$ is preferably selected from the group consisting of straight-chain or branched, $C_{1-8}$-alkyl groups.

$R^3$ is preferably selected from the group consisting of straight-chain or branched $C_{2-8}$-alkyl and alicyclic $C_{3-8}$-alkyl groups.

Alternatively, $R^2$ and $R^3$ together with the nitrogen atom to which they are attached or with further atoms may preferably form a five- to six-membered ring.

$R^4$ is preferably selected from the group consisting of:
halogen atoms (—X);
straight-chain or branched $C_{1-8}$-alkyl groups or
straight-chain or branched $C_{1-5}$-haloalkyl groups.

$R^5$ is preferably selected from the group consisting of:
halogen atoms (—X);
straight-chain or branched $C_{1-8}$-alkyl groups or
straight-chain or branched $C_{1-5}$-haloalkyl groups.

$R^6$ is preferably selected from the group consisting of straight-chain or branched $C_{2-8}$-alkyl groups.

$R^7$ is preferably selected from groups (i) to (iii)
(i) groups of the formulae (II-a) to (II-e),

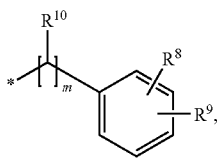

(II-a)

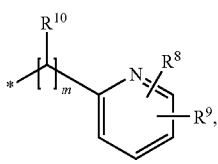

(II-b)

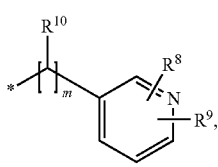

(II-c)

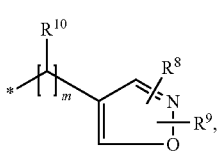

(II-d)

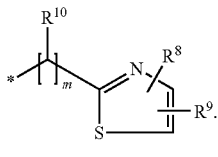

(II-e)

In formulae (II-a) to (II-e), the radicals have the following meanings:
* denotes the bond to the Y atom.
m preferably represents 0 or 1.
$R^8$ is preferably selected from the group consisting of hydrogen, Cl, F or Br, $C_{1-8}$-alkyl, $C_{6-12}$-aryl, $C_{7-16}$-alkylaryl or $C_{7-16}$-aralkyl groups.
$R^9$ is preferably selected from the group consisting of hydrogen, Cl, F or Br, $C_{1-8}$-alkyl, $C_{6-12}$-aryl, $C_{7-16}$-alkylaryl or $C_{7-16}$-aralkyl groups.

Alternatively, $R^8$ and $R^9$ together with the skeleton atoms to which they are attached or optionally with one, two or more atoms, preferably selected from the group consisting of N, O and S, may form a five- to six-membered ring.

$R^{10}$ is preferably selected from the group consisting of hydrogen, straight-chain or branched $C_{1-8}$-alkyl groups.

(iii) In a further preferred embodiment of the present invention, $R^7$ is selected from among radicals of the formula (III)

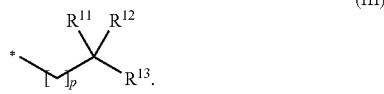

(III)

In formula (III), the radicals have the following meanings:
* denotes the bond to the Y atom.
p represents 0 or 1.
$R^{11}$ is selected from the group consisting of hydrogen, straight-chain or branched $C_{1-8}$-alkyl, $C_{2-8}$-alkenyl, $C_{2-8}$-alkynyl groups or cyclic $C_{3-8}$-alkyl, $C_{4-8}$-alkenyl, $C_{4-8}$-alkynyl groups.
$R^{12}$ is selected from the group consisting of hydrogen, straight-chain or branched $C_{1-8}$-alkyl, $C_{2-8}$-alkenyl, $C_{2-8}$-alkynyl groups or cyclic $C_{3-8}$-alkyl, $C_{4-8}$-alkenyl, $C_{4-8}$-alkynyl groups.
$R^{13}$ is selected from the group consisting of hydrogen, straight-chain or branched $C_{1-8}$-alkyl, $C_{2-8}$-alkenyl, $C_{2-8}$-alkynyl groups or cyclic $C_{3-8}$-alkyl, $C_{4-8}$-alkenyl, $C_{4-8}$-alkynyl groups.

In the formula (I), the radicals have the particularly preferred meanings defined below. The definitions given as being particularly preferred likewise apply to all intermediates:
Y particularly preferably represents oxygen.
$R^1$ is particularly preferably selected from the group consisting of
hydrogen,
methyl and ethyl.
$R^2$ is particularly preferably selected from the group consisting of methyl and ethyl.
$R^3$ is particularly preferably selected from the group consisting of methyl and cyclopropyl.
Alternatively, $R^2$ and $R^3$ together with the nitrogen atom to which they are attached particularly preferably form a piperidyl or pyrrolidyl ring.
$R^4$ is particularly preferably selected from Cl and F atoms and —$CF_3$, —$CF_2H$ and methyl groups.
$R^5$ is particularly preferably selected from Cl and F atoms and —$CF_3$, —$CF_2H$ and methyl groups.
$R^6$ is particularly preferably selected from the group consisting of hydrogen, methyl and ethyl.
$R^7$ is particularly preferably selected from the groups (i) to (iii):
(i) groups of the formulae (II-f) to (II-j) which may be substituted by one or two N, O or S atoms.

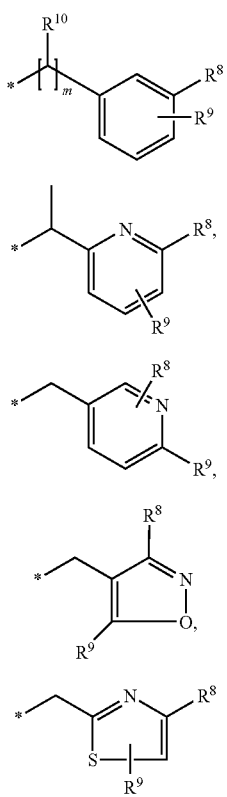

In the formulae (II-f) to (II-j), the radicals have the following meanings:
* denotes the bond to the Y atom.
m represents 0 or 1.
$R^8$ is selected from the group consisting of hydrogen, chlorine, fluorine, bromine; methyl, trifluoromethyl, t-butyl and phenoxy.
$R^9$ is selected from the group consisting of hydrogen, chlorine, fluorine, bromine; methyl, trifluoromethyl, t-butyl and phenoxy.
Alternatively, $R^8$ and $R^9$ together with the skeleton atoms to which they are attached particularly preferably may form a five- or six-membered ring.
$R^{10}$ particularly preferably represents hydrogen and methyl.
  (ii) In an alternative particularly preferred embodiment of the present invention, $R^7$ is selected from the group consisting of 2-(trimethylsilyl)ethyl, ethyl, allyl, n-propyl, 3-methylbut-2-en-1-yl, but-2-ynyl, 3-phenylprop-2-en-1-yl, 2-methoxyethoxy)methyl, cyclopentyl, 1-methylprop-2-yn-1-yl and 2-methylprop-2-en-1-yl
  (iii) In a further alternative particularly preferred embodiment of the present invention, $R^7$ is selected from among radicals of the formula (III)

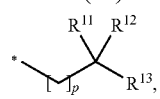

(III)

in which
p represents 0 or 1.
$R^{11}$ is selected from the group consisting of hydrogen, methyl, ethyl, cyclopropyl and trifluoromethyl.
$R^{12}$ is selected from the group consisting of hydrogen, methyl, ethyl, cyclopropyl and trifluoromethyl.
$R^{13}$ is selected from the group consisting of hydrogen, methyl, ethyl, cyclopropyl and trifluoromethyl.

Depending on the nature of the substituents defined above, the amidines according to the invention have acidic or basic properties and can form salts, if appropriate also internal salts or adducts, with inorganic or organic acids or with bases or with metal ions.

Suitable metal ions are in particular the ions of the elements of the second main group, in particular calcium and magnesium, of the third and fourth main group, in particular aluminum, tin and lead, and of the first to eighth subgroups, in particular chromium, manganese, iron, cobalt, nickel, copper, zinc and others. Particular preference is given to the metal ions of the elements of the fourth period. Here, the metals can be present in the various valencies that they can assume.

If the compounds of the formula (I) carry hydroxyl groups, carboxyl groups or other groups inducing acidic properties, these compounds can be reacted with bases to give salts.

Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having ($C_1$-$C_4$)-alkyl groups, mono-, di- and trialkanolamines of ($C_1$-$C_4$)-alkanols, choline and also chlorocholine.

If the compounds of the formula (I) carry amino groups, alkylamino groups or other groups which induce basic properties, these compounds can be reacted with acids to give salts.

Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as $NaHSO_4$ and $KHSO_4$.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl groups having 1 to 20 carbon atoms), arylsulfonic acids or -disulfonic acids (aromatic radicals, such as phenyl and naphthyl, which carry one or two sulfonic acid groups), alkylphosphonic acids (phosphonic acids having straight-chain or branched alkyl groups having 1 to 20 carbon atoms), arylphosphonic acids or -diphosphonic acids (aromatic radicals, such as phenyl and naphthyl, which carry one or two phosphonic acid radicals), where the alkyl and aryl radicals may carry further substituents, for example p-toluenesulfonic acid, salicylic acid, p-aminosalicylic acid, 2-phenoxybenzoic acid, 2-acetoxybenzoic acid, etc.

The salts obtainable in this manner also have fungicidal properties.

Amidines particularly preferred in connection with the present invention are selected from the group consisting of N'-{4-[(E)-{[(2,4-dimethylbenzyl)oxy]imino}methyl]-2,5-dimethylphenyl}-N,N-dimethylimidoformamide (1), N'-{2,5-dimethyl-4-[(E)-({[3-(trifluoromethyl)benzyl]oxy}-imino)methyl]phenyl}-N,N-dimethylimidoformamide (2), N'-(4-{(E)-[(benzyloxy)imino]methyl}-2,5-di-methylphenyl)-N-ethyl-N-methylimidoformamide (3), N'-(4-{(E)-[(4H-1,3-benzodioxin-7-ylmethoxy)imino]methyl}-2,5-dimethylphenyl)-N-ethyl-N-methylimidoformamide (4), N'-{4-[(E)-{[(2-chlorobenzyl)oxy]imino}methyl]-2,5-dimethylphenyl}-N-ethyl-N-methylimidoformamide (5), N'-{2,5-dimethyl-4-[(E)-{[(2-methylprop-2-en-1-yl)oxy]imino}methyl]phenyl}-N-ethyl-N-methylimidoformamide (6), N'-{4-[(E)-{[(2,4-dichlorobenzyl)oxy]imino}methyl]-2, 5-dimethylphenyl}-N-ethyl-N-methylimidoformamide (7), N'-{4-[(E)-{[(3,5-dichlorobenzyl)oxy]imino}methyl]-2,5-di-methylphenyl}-N-ethyl-N-methylimidoformamide (8), N-ethyl-N'-{4-[(1E)-N-tert-butoxyethanimidoyl]-2,5-dimethylphenyl}-N-methylimidoformamide (9), N-ethyl-N'-{4-[(1E)-N-isopropoxyethanimidoyl]-2,5-dimethylphenyl}-N-methylimidoformamide (10), N'-{2,5-dimethyl-4-[(1E)-N-phenoxyethanimidoyl]-phenyl}-N-ethyl-N-methylimidoformamide (11), N'-(4-{(1E)-N-[(4-tert-butylbenzyl)oxy]ethanimidoyl}-2,5-dimethylphenyl)-N-ethyl-N-methylimidoformamide (12), N-ethyl-N'-{4-[(1E)-N-isobutoxyethanimidoyl]-2,5-dimethylphenyl}-N-methylimidoformamide (13), N'-{4-[(1E)-N-(cyclopentyloxy)ethanimidoyl]-2,5-dimethylphenyl}-N-ethyl-N-methylimidoformamide (14), N'-(2,5-dimethyl-4-{(1E)-N-[(1-methylprop-2-yn-1-yl)oxy]ethanimidoyl}phenyl)-N-ethyl-N-methylimidoformamide (15), N'-{4-[(1E)-N-(but-2-yn-1-yloxy)ethanimidoyl]-2,5-dimethylphenyl}-N-ethyl-N-methylimidoformamide (16), N'-{2,5-dimethyl-4-[(1E)-N-(2,2,2-trifluoroethoxy)ethanimidoyl]phenyl}-N-ethyl-N-methylimidoformamide (17), N'-{2,5-dimethyl-4-[(1E)-1-methyl-3,5,8-trioxa-2-azanon-1-en-1-yl]phenyl}-N-ethyl-N-methylimidoformamide (18), N'-{2,5-dimethyl-4-[(1E)-N-{[(2E)-3-phenylprop-2-en-1-yl]oxy}ethanimidoyl]phenyl}-N-ethyl-N-methylimidoformamide (19), N'-{4-[(1E)-N-(dicyclopropylmethoxy)ethanimidoyl]-2,5-dimethylphenyl}-N-ethyl-N-methylimidoformamide (20), N'-(2,5-dimethyl-4-{(E)-N-[(4-phenyl-1,3-thiazol-2-yl)meth-oxy]ethanimidoyl}phenyl)-N-ethyl-N-methylimidoformamide (21), N'-(2,5-dimethyl-4-{(1E)-N-[(3-phenoxybenzyl)oxy]ethanimidoyl}phenyl)-N-ethyl-N-methylimidoformamide (22), N-ethyl-N'-{4-[(1E)-N-ethoxyethanimidoyl]-2,5-dimethylphenyl}-N-methylimidoformamide (23), N-ethyl-N'-{4-[(1E)-N-methoxyethanimidoyl]-2,5-dimethylphenyl}-N-methylimidoformamide (24), N'-(4-{(1E)-N-[2-(4-chlorophenyl)ethoxy]ethanimidoyl}-2,5-dimethylphenyl)-N-ethyl-N-methylimidoformamide (25), N-ethyl-N'-{4-[(E)-{[(4-fluorobenzyl)oxy]ethanimidoyl}-2,5-dimethylphenyl}-N-methylimidoformamide (26), N'-(2,5-dimethyl-4-{(E)-[1-phenylethoxy]ethanimidoyl}phenyl)-N-ethyl-N-methylimidoformamide (27), N'-(2,5-dimethyl-4-{(1E)-N-[1-(6-methylpyridin-2-yl)ethoxy]ethanimidoyl}phenyl)-N-ethyl-N-methylimidoformamide (28), N'-(4-{(1E)-N-[(2,6-dichlorobenzyl)oxy]ethanimidoyl}-2,5-dimethylphenyl)-N-ethyl-N-methylimidoformamide (29), N'-(4-{(E)-N-[(3,4-dichlorobenzyl)oxy]-ethanimidoyl}-2,5-dimethylphenyl)-N-ethyl-N-methylimidoformamide (30), N'-(4-{(1E)-N-[benzyloxy]-ethanimidoyl}-2,5-dimethylphenyl)-N-ethyl-N-methylimidoformamide (31), N'-(4-{(1E)-N-[(6-chloropyridin-3-yl)methoxy]ethanimidoyl}-2,5-dimethylphenyl)-N-ethyl-N-methylimidoformamide (32), N'-(2,5-dimethyl-4-{(1E)-N-[(3-methylbut-2-en-1-yl)oxy]ethanimidoyl}phenyl)-N-ethyl-N-methylimidoformamide (33), N'-{2,5-dimethyl-4-[(1E)-N-{2-[3-(trifluoromethyl)phenoxy]ethoxy}ethan-imidoyl]phenyl}-N-ethyl-N-methylimidoformamide (34), N'-{4-[(1E)-N-(allyloxy)ethanimidoyl]-2,5-dimethylphenyl}-N-ethyl-N-methylimidoformamide (35), N'-(4-{(1E)-N-[(3,5-dimethylisoxazol-4-yl)methoxy]ethanimidoyl}-2,5-dimethylphenyl)-N-ethyl-N-methylimidoformamide (36), N'-{4-[(1E)-N-(n-propoxy)ethanimidoyl]-2,5-dimethylphenyl}-N-ethyl-N-methylimidoformamide (37), N'-(4-{(1E)-N-[1-(4-chlorophenyl)ethoxy]ethanimidoyl}-2,5-dimethylphenyl)-N-ethyl-N-methylimidoformamide (38), N'-{4-[(E)-(tert-butoxyimino)methyl]-2,5-dimethylphenyl}-N-ethyl-N-methylimidoformamide (39), N-ethyl-N'-{4-[(E)-(isopropoxyimino)methyl]-2,5-dimethylphenyl}-N-methylimidoformamide (40), N'-(2,5-dimethyl-4-{(1E)-N-[2-(trimethylsilyl)ethoxy]ethanimidoyl}phenyl)-N-ethyl-N-methylimidoformamide (41), N'-(4-{(E)-[(4-tert-butylphenoxy)imino]methyl}-2,5-dimethylphenyl)-N-ethyl-N-methylimidoformamide (42), N'-{2,5-dimethyl-4-[(1E)-N-{2-[3-(trifluoromethyl)phenoxy]ethoxy}-ethanimidoyl]phenyl}-N-ethyl-N-methylimidoformamide (43), N'-(2,5-dimethyl-4-{(1E)-N-[2-(trimethylsilyl)ethoxy]ethanimidoyl}phenyl)-N-ethyl-N-methylimidoformamide (44), N-ethyl-N'-(4-{(1E)-1-[2-(2-fluorophenyl)hydrazinylidene]ethyl}-2,5-dimethylphenyl)-N-methylimidoformamide (45), N'-{4-[(1E)-N-(4,4-dimethylpentyl)ethanimidoyl]-2,5-dimethylphenyl}-N-ethyl-N-methylimidoformamide (46), N'-(4-{(E)-[(cyclopropylmethoxy)imino]methyl}-2,5-dimethylphenyl)-N-ethyl-N-methylimidoformamide (47), N'-(4-{(E)-[(3,3-dimethylbutoxy)imino]methyl}-2,5-dimethylphenyl)-N-ethyl-N-methylimidoformamide (48).

Preparation of the Amidines According to the Invention

The amidines according to the invention can be obtained by the process shown in scheme (I) below:

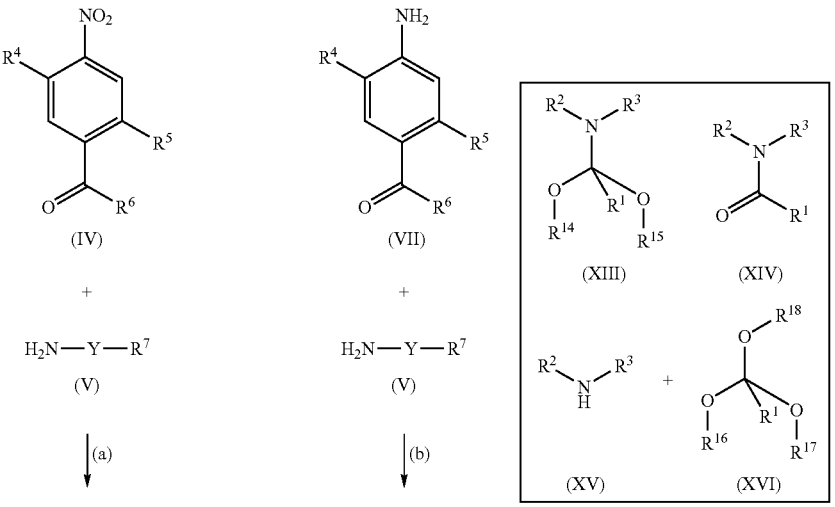

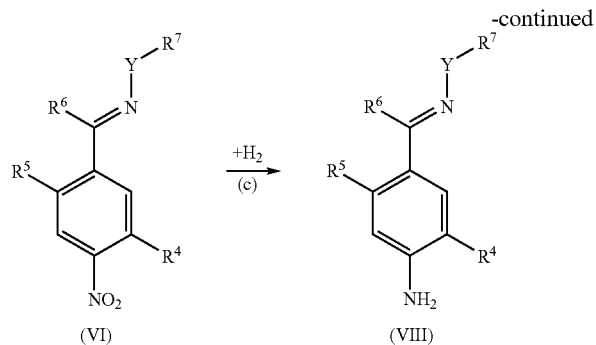

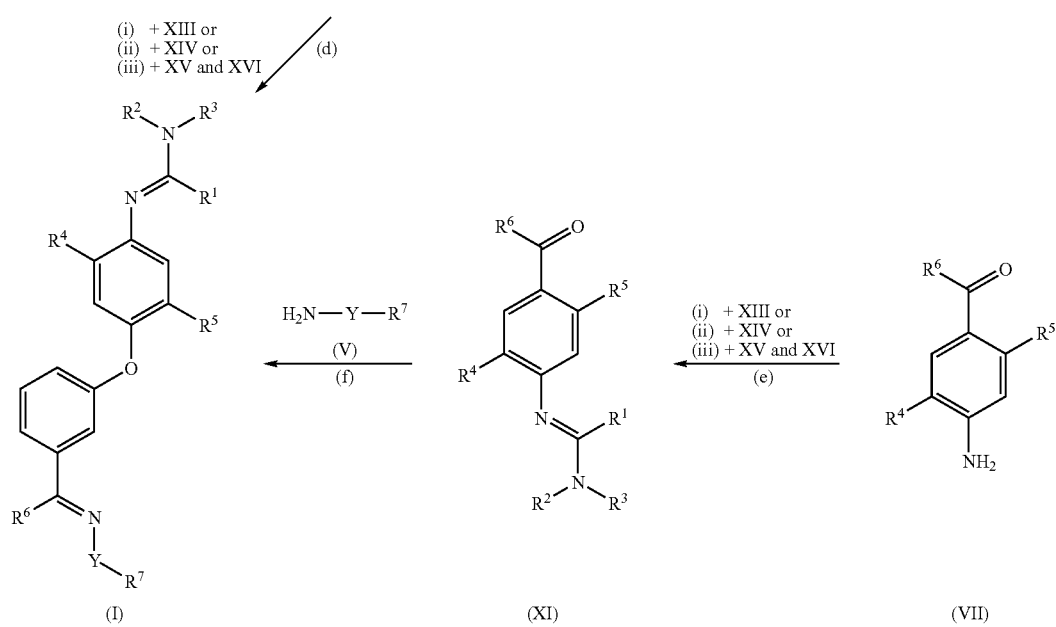

Step (a)

In one embodiment according to the invention, nitrobenzaldehydes ($R^6$=H) or nitrobenzoketones ($R^6 \neq$H) of the formula (IV) are reacted with amines of the formula (V) in accordance with the reaction scheme below to give nitroaromatics of the formula (VI):

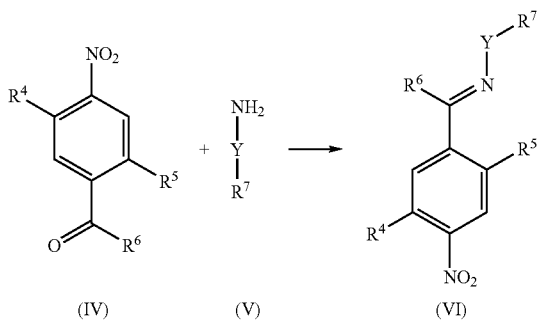

The nature of the primary amines of the formula (V) is essentially determined by group Y. The connections can be seen in Table I below.

TABLE I

| Y | prim. amine (V) | substituted phenylamidine (I) |
|---|---|---|
| NH | hydrazine | hydrazone-substituted phenylamidine (I) |
| O | hydroxylamine | oxime ether-substituted phenylamidine (I) |
| Single bond | prim. amine | Azomethine-substituted phenylamidine (I) |

The hydrazines of the formula (V) used for preparing hydrazone-substituted phenylamidines of the formula (I) are selected, for example, from the group of N-arylhydrazines, N-benzylhydrazines and N-alkylhydrazines.

The hydroxylamines of the formula (V) used for preparing oxime ether-substituted phenylamidines of the formula (I) are selected, for example, from the group consisting of O-arylhydroxylamines, O-benzylhydroxylamines and N-alkylhydroxylamines.

The primary amines of the formula (V) used for preparing azomethine-substituted phenylamidines of the formula (I) are selected, for example, from the group consisting of anilines, benzylamines and primary alkylamines.

The reaction is preferably carried out in the presence of a base.

Suitable bases are organic and inorganic bases which are usually used in such reactions. Preference is given to using bases which, for example, are selected from the group consisting of hydrides, hydroxides, amides, alkoxides, acetates, fluorides, phosphates, carbonates and bicarbonates of alkali metals or alkaline earth metals. Particular preference is given here to sodium amide, sodium hydride, lithium diisopropylamide, sodium methoxide, potassium tert-butoxide, sodium hydroxide, potassium hydroxide, sodium acetate, sodium phosphate, potassium phosphate, potassium fluoride, cesium fluoride, sodium carbonate, potassium carbonate, potassium bicarbonate, sodium bicarbonate and cesium carbonate. Furthermore, tertiary amines, such as, for example, trimethylamine, triethylamine, tributylamine, N,N-dimethylaniline, N,N-dimethylbenzylamine, pyridine, N-methylpiperidine, N-methylpyrolidone, N,N-dimethylaminopyridine, diazabicyclooctane (DABCO), diazabicyclononene (DBN) and diazabicycloundecene (DBU).

If appropriate, a catalyst chosen from the group consisting of palladium, copper and their salts or complexes may be used.

The reaction of the nitrobenzene derivative with the phenol can be carried out neat or in a solvent; preferably, the reaction is carried out in a solvent selected from standard solvents which are inert under the prevailing reaction conditions.

Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisole; nitrites, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; or mixtures of these with water, and also pure water.

The reaction can be carried out under reduced pressure, at atmospheric pressure or under superatmospheric pressure and at temperatures of from −20 to 200° C.; preferably, the reaction is carried out at atmospheric pressure and temperatures of from 50 to 150° C.

Step (b)

In an alternative embodiment according to the invention, aminobenzaldehyes or aminobenzoketones of the formula (VII) are reacted with amines of the formula (V) in accordance with the reaction scheme below to give anilines of the formula (VIII):

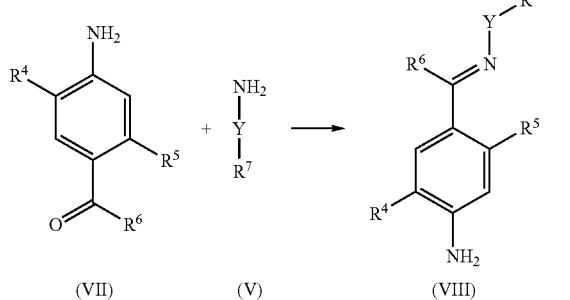

With regard to the reaction conditions, the solvents, the catalysts and the nature of the amines of the formula (V), reference may be made to step (a).

Step (c)

The nitroaromatics of the formula (VI) obtained in steps (a) and (b) can be reduced in accordance with the reaction scheme below to give the anilines of the formula (VIII):

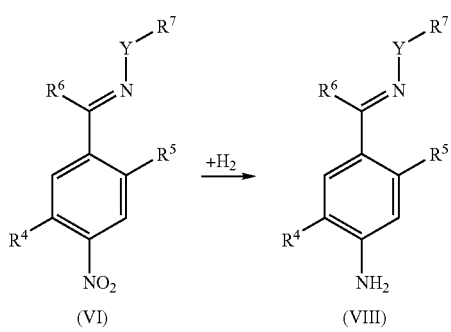

The reduction according to step (c) can be carried out by any methods for reducing nitro groups described in the prior art.

Preferably, the reduction is carried out using tin chloride in concentrated hydrochloric acid, as described in WO 0046184. However, alternatively, the reduction can also be carried out by using hydrogen gas, preferably in the presence of suitable hydrogenation catalysts, such as, for example, Raney nickel, Pd/C. The reaction conditions have already been described in the prior art and are familiar to the person skilled in the art.

If the reduction is carried out in the liquid phase, the reaction should take place in a solvent inert to the prevailing reaction conditions. One such solvent is, for example, toluene.

Step (d)

The conversion of the anilines of the formula (VIII) into the amidines of the formula (I) according to the invention according to step (d) can be carried out, as shown above in schema (I), using different alternative methods employing
(i) aminoacetals of the formula (XIII) or
(ii) amides of the formula (XIV) or
(iii) amines of the formula (XV) in the presence of ortho esters of the formula (XVI) according to the reaction scheme below:

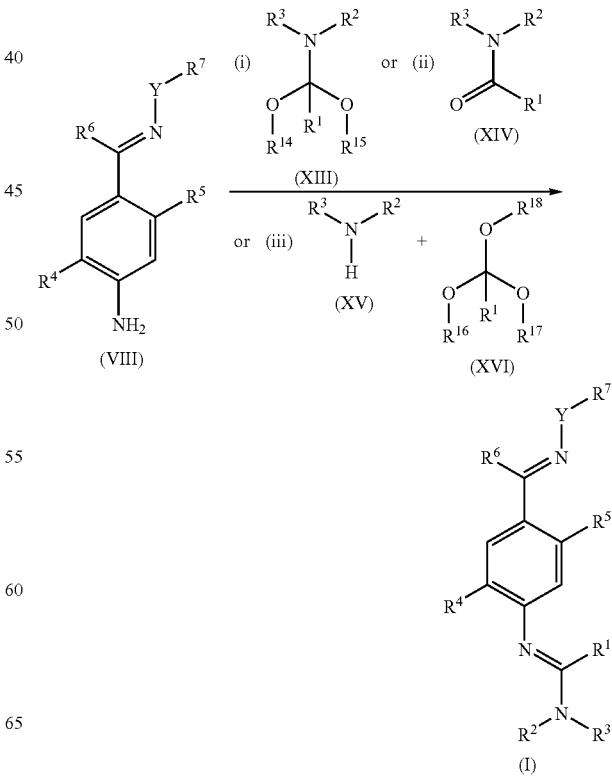

The individual alternative embodiments (i) to (iii) of the process according to the invention are briefly illustrated below:

(i) According to one embodiment according to the invention, shown in scheme (I) as step (i), the anilines of the formula (VIII) are reacted with aminoacetals of the formula (XIII) in which $R^2$ and $R^3$ are defined as described above and $R^{14}$ and $R^{15}$ are selected from the group consisting of $C_{1-8}$-alkyl groups, preferably from $C_{2-6}$-alkyl groups, particularly preferably from $C_{3-5}$-alkyl groups, and which together with the oxygen atoms to which they are attached may form a five- or six-membered ring, to give the amidines of the formula (I) according to the invention.

The aminoacetals of the formula (XIII) can be obtained from the formamides described in JACS, 65, 1566 (1943), by reaction with alkylating agents, such as, for example, dimethyl sulfate.

The reaction according to step (i) is preferably carried out in the presence of an acid.

Suitable acids are, for example, selected from the group consisting of organic and inorganic acids, and preference is given to p-toluenesulfonic acid, methanesulfonic acid, hydrochloric acid (gaseous, aqueous or in organic solution) or sulfuric acid.

(ii) In an alternative embodiment according to the invention, shown in scheme (I) as step (ii), the anilines of the formula (VIII) are reacted with amides of the formula (XIV) in which the radicals $R^1$ to $R^3$ are as defined above to give the amidines according to the invention.

The reaction according to step (ii) is, if appropriate, carried out in the presence of a halogenating agent. Suitable halogenating agents are, for example, selected from the group consisting of $PCl_5$, $PCl_3$, $POCl_3$ or $SOCl_2$.

Moreover, the reaction may alternatively be carried out in the presence of a condensing agent.

Suitable condensing agents are those usually employed for forming amide bonds; acid halide formers, such as, for example, phosgene, phosphorus tribromide, phosphorus trichloride, phosphorus pentachloride, phosphorus oxytrichloride or thionyl chloride; anhydride formers, such as, for example, chloroformate, methyl chloroformate, isopropyl chloroformate, isobutyl chloroformate or methanesulfonyl chloride; carbodiimines, such as, for example, N,N'-dicyclohexylcarbodiimine (DCC) or other customary condensing agents, such as, for example, phosphorus pentoxide, polyphosphoric acid, N,N'-carbodiimidazole, 2-ethoxy-N-ethoxycarbonyl-1,2-dihydroquinoline (EEDQ), triphenylphosphine/carbon tetrachloride or bromo-tripyrrolidinophosphonium hexafluorophosphate may be mentioned by way of examples.

The reaction according to step (ii) is preferably carried out in a solvent selected from standard solvents which are inert under the prevailing reaction conditions. Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisole; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; esters, such as, for example, methyl acetate or ethyl acetate; sulfoxides, such as, for example, dimethyl sulfoxide (DMSO); sulfones, such as, for example, sulfolane; alcohols, such as, for example, methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether or mixtures of these.

(iii) According to a further alternative embodiment according to the invention shown in scheme (I) as step (iii), the anilines of the formula (VIII) are reacted with amines of the formula (XV) in which the radicals $R^2$ and $R^3$ are as defined above in the presence of ortho esters of the formula (XVI), in which $R^1$ is as defined above and $R^{16}$ to $R^{18}$ independently of one are selected from the group consisting of $C_{1-8}$-alkyl groups, preferably from $C_{2-6}$-alkyl groups, particularly preferably from $C_{3-5}$-alkyl groups, which together with the oxygen atoms to which they are attached may form a five- or six-membered ring, to give the amidines according to the invention.

The reaction according to step (iii) is preferably carried out in a solvent selected from standard solvents which are inert under the prevailing reaction conditions. Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisole; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylene phosphoric triamide; esters, such as, for example, methyl acetate or ethyl acetate; sulfoxides, such as, for example, dimethyl sulfoxide (DMSO); sulfones, such as, for example, sulfolane; alcohols, such as, for example, methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether; or mixtures of these with water, and also pure water.

Step (e)

In an alternative embodiment according to the invention, it is already possible to react the aminobenzaldehydes or aminobenzoketones of the formula (VII)

(i) with aminoacetals of the formula (XIII) or
(ii) with amides of the formula (XIV) or
(iii) with amines of the formula (XV) in the presence of ortho esters of the formula (XVI)

in accordance with the reaction scheme below to give amidines of the formula (X):

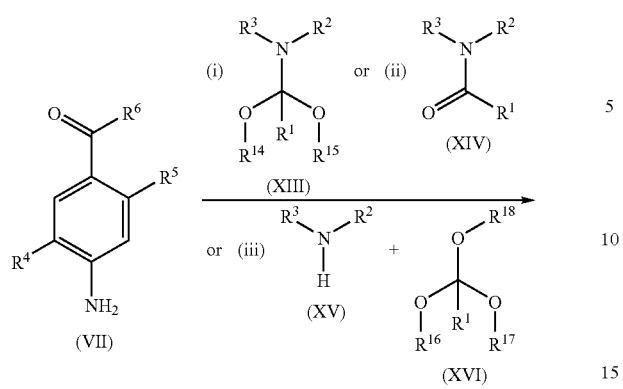 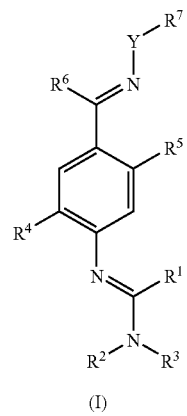

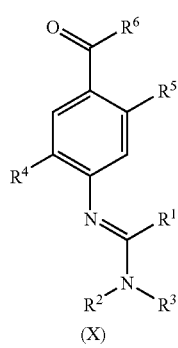

With regard to the reaction conditions, solvents, catalysts, reference may be made to step (d).

The further conversion of the amidines of the formula (X) into the target molecules of the formula (I) according to the invention can be carried out, for example, as described in step (f).

Step (f)

According to a further embodiment according to the invention, the amidines of the formula (X) obtainable from step (e) can be reacted with amidines of the formula (V) to give the target molecules of the formula (I) according to the invention, in accordance with the reaction scheme below:

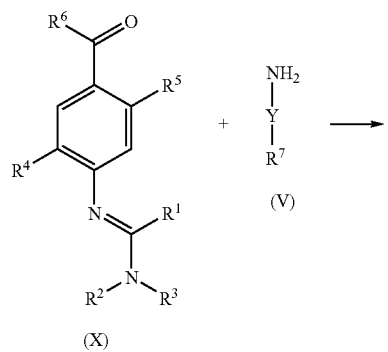

With regard to the reaction conditions, solvents and catalysts and the nature of the amine (V), reference may be made to step (a).

In connection with the processes according to the invention for preparing the amidines of the formula (I), the following combinations of reaction steps are to be regarded as advantageous: steps (a) and (c); steps (b) and (d); steps (c) and (f); steps (e) and (f) and steps (a), (c) and (d).

The preparation of the amidines according to the invention is preferably carried out without intermediate isolation of the intermediates.

The final purification of the amidines can be carried out using customary purification methods. Preferably, purification is carried out by crystallization.

Controlling of Undesirable Microorganisms

The amidines according to the invention exhibit a strong microbicidal action and can be used for controlling undesirable microorganisms, such as fungi and bacteria, in plant protection and in material protection.

Fungicides can be used in plant protection for controlling Plasmodiophoromycetes, Oomycetes, Chytridiomycetes, Zygomycetes, Ascomycetes, Basidiomycetes and Deuteromycetes.

Bactericides can be used in plant protection for controlling Pseudomonadaceae, Rhizobiaceae, Enterobacteriaceae, Corynebacteriaceae and Streptomycetaceae.

Mention may be made, by way of example but without limitation, of some pathogens of fungal and bacterial diseases which come under the generic terms listed above:

diseases caused by pathogens of powdery mildew, such as, for example,

*Blumeria* species, such as, for example, *Blumeria graminis;*

*Podosphaera* species, such as, for example, *Podosphaera leucotricha;*

*Sphaerotheca* species, such as, for example, *Sphaerotheca fuliginea;*

*Uncinula* species, such as, for example, *Uncinula necator;* diseases caused by rust pathogens, such as, e.g.,

*Gymnosporangium* species, such as, for example, *Gymnosporangium sabinae;*

*Hemileia* species, such as, for example, *Hemileia vastatrix;*

*Phakopsora* species, such as, for example, *Phakopsora pachyrhizi* and *Phakopsora meibomiae;*

*Puccinia* species, such as, for example, *Puccinia recondita;*

*Uromyces* species, such as, for example, *Uromyces appendiculatus;* diseases caused by pathogens of the Oomycetes group, such as, e.g.,
*Bremia* species, such as, for example, *Bremia lactucae*;
*Peronospora* species, such as, for example, *Peronospora pisi* or *P. brassicae*;
*Phytophthora* species, such as, for example, *Phytophthora infestans*;
*Plasmopara* species, such as, for example, *Plasmopara viticola*;
*Pseudoperonospora* species, such as, for example, *Pseudoperonospora humuli* or *Pseudoperonospora cubensis*;
*Pythium* species, such as, for example, *Pythium ultimum*;
leaf spot diseases and leaf wilts caused by, e.g.,
*Alternaria* species, such as, for example, *Alternaria solani*;
*Cercospora* species, such as, for example, *Cercospora beticola*;
*Cladosporium* species, such as, for example, *Cladosporium cucumerinum*;
*Cochliobolus* species, such as, for example, *Cochliobolus sativus*
(conidial form: *Drechslera*, syn: *Helminthosporium*);
*Colletotrichum* species, such as, for example, *Colletotrichum lindemuthanium*;
*Cycloconium* species, such as, for example, *Cycloconium oleaginum*;
*Diaporthe* species, such as, for example, *Diaporthe citri*;
*Elsinoe* species, such as, for example, *Elsinoe fawcettii*;
*Gloeosporium* species, such as, for example, *Gloeosporium laeticolor*;
*Glomerella* species, such as, for example, *Glomerella cingulata*;
*Guignardia* species, such as, for example, *Guignardia bidwelli*;
*Leptosphaeria* species, such as, for example, *Leptosphaeria maculans*;
*Magnaporthe* species, such as, for example, *Magnaporthe grisea*;
*Mycosphaerella* species, such as, for example, *Mycosphaerella graminicola* and *Mycosphaerella fijiensis*;
*Phaeosphaeria* species, such as, for example, *Phaeosphaeria nodorum*;
*Pyrenophora* species, such as, for example, *Pyrenophora teres*;
*Ramularia* species, such as, for example, *Ramularia collocygni*;
*Rhynchosporium* species, such as, for example, *Rhynchosporium secalis*;
*Septoria* species, such as, for example, *Septoria apii*;
*Typhula* species, such as, for example, *Typhula incamata*;
*Venturia* species, such as, for example, *Venturia inaequalis*;
root and stalk diseases caused by, e.g.,
*Corticium* species, such as, for example, *Corticium graminearum*;
*Fusarium* species, such as, for example, *Fusarium oxysporum*;
*Gaeumannomyces* species, such as, for example, *Gaeumannomyces graminis*;
*Rhizoctonia* species, such as, for example, *Rhizoctonia solani*;
*Tapesia* species, such as, for example, *Tapesia acuformis*;
*Thielaviopsis* species, such as, for example, *Thielaviopsis basicola*;
ear and panicle diseases (including maize cobs) caused by, e.g.,
*Alternaria* species, such as, for example, *Alternaria* spp.;
*Aspergillus* species, such as, for example, *Aspergillus flavus*;
*Cladosporium* species, such as, for example, *Cladosporium cladosporioides*;
*Claviceps* species, such as, for example, *Claviceps purpurea*;
*Fusarium* species, such as, for example, *Fusarium culmorum*;
*Gibberella* species, such as, for example, *Gibberella zeae*;
*Monographella* species, such as, for example, *Monographella nivalis*;
diseases caused by smuts, such as, e.g.,
*Sphacelotheca* species, such as, for example, *Sphacelotheca reiliana*;
*Tilletia* species, such as, for example, *Tilletia caries*;
*Urocystis* species, such as, for example, *Urocystis occulta*;
*Ustilago* species, such as, for example, *Ustilago nuda*;
fruit rot caused by, e.g.,
*Aspergillus* species, such as, for example, *Aspergillus flavus*;
*Botrytis* species, such as, for example, *Botrytis cinerea*;
*Penicillium* species, such as, for example, *Penicillium expansum* and *Penicillium purpurogenum*;
*Sclerotinia* species, such as, for example, *Sclerotinia sclerotiorum*;
*Verticilium* species, such as, for example, *Verticilium alboatrum*;
seed- and soil-borne rots and wilts, and seedling diseases, caused by, e.g.,
*Alternaria* species, such as, for example, *Alternaria brassicicola*;
*Aphanomyces* species, such as, for example, *Aphanomyces euteiches*;
*Ascochyta* species, such as, for example, *Ascochyta lentis*;
*Aspergillus* species, such as, for example, *Aspergillus flavus*;
*Cladosporium* species, such as, for example, *Cladosporium herbarum*;
*Cochliobolus* species, such as, for example, *Cochliobolus sativus*
(conidial form: *Drechslera*, *Bipolaris* syn: *Helminthosporium*);
*Colletotrichum* species, such as, for example, *Colletotrichum coccodes*;
*Fusarium* species, such as, for example, *Fusarium culmorum*;
*Gibberella* species, such as, for example, *Gibberella zeae*;
*Macrophomina* species, such as, for example, *Macrophomina phaseolina*;
*Monographella* species, such as, for example, *Monographella nivalis*;
*Penicillium* species, such as, for example, *Penicillium expansum*;
*Phoma* species, such as, for example, *Phoma lingam*;
*Phomopsis* species, such as, for example, *Phomopsis sojae*;
*Phytophthora* species, such as, for example, *Phytophthora cactorum*;
*Pyrenophora* species, such as, for example, *Pyrenophora graminea*;
*Pyricularia* species, such as, for example, *Pyricularia oryzae*;
*Pythium* species, such as, for example, *Pythium ultimum*;
*Rhizoctonia* species, such as, for example, *Rhizoctonia solani*;
*Rhizopus* species, such as, for example, *Rhizopus oryzae*;

*Sclerotium* species, such as, for example, *Sclerotium rolfsii;*

*Septoria* species, such as, for example, *Septoria nodorum; Typhula* species, such as, for example, *Typhula incamata; Verticillium* species, such as, for example, *Verticillium dahliae;* cankers, galls and witches' broom disease caused by, e.g., *Nectria* species, such as, for example, *Nectria galligena;* wilts caused by, e.g.,

*Monilinia* species, such as, for example, *Monilinia laxa;* deformations of leaves, flowers and fruits caused by, e.g., *Taphrina* species, such as, for example, *Taphrina deformans;* degenerative diseases of woody plants caused by, e.g., *Esca* species, such as, for example, *Phaeomoniella chlamydospora, Phaeoacremonium aleophilum* and *Fomitiporia mediterranea;* flower and seed diseases caused by, e.g., *Botrytis* species, such as, for example, *Botrytis cinerea;* diseases of plant tubers caused by, e.g.,

*Rhizoctonia* species, such as, for example, *Rhizoctonia solani;*

*Helminthosporium* species, such as, for example, *Helminthosporium solani;* diseases caused by bacterial pathogens, such as, e.g., *Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora.*

Preferably, the following diseases of soybeans can be combated:

fungal diseases on leaves, stalks, pods and seeds caused by, e.g., alternaria leaf spot (*Alternaria* spec. atrans tenuissima), anthracnose (Colletotrichum gloeosporoides dematium var. *truncatum*), brown spot (*Septoria glycines*), cercospora leaf spot and blight (*Cercospora kikuchii*), choanephora leaf blight (*Choanephora infundibulifera trispora* (Syn.)), *dactuliophora* leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

fungal diseases on roots and the stem base caused by, e.g., black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also exhibit a strong strengthening activity in plants. They are accordingly suitable for mobilizing intrinsic defenses of plants against attack by undesirable microorganisms.

In the present context, plant-strengthening (resistance-inducing) compounds are to be understood as meaning those materials which are capable of stimulating the defense system of plants such that the treated plants, on subsequent inoculation with undesirable microorganisms, exhibit extensive resistance to these microorganisms.

In the present case, undesirable microorganisms are to be understood as meaning phytopathogenic fungi, bacteria and viruses. The substances according to the invention can thus be used to protect plants from attack by the harmful pathogens mentioned for a certain period of time after the treatment. The period of time for which protection is brought about generally ranges from 1 to 10 days, preferably 1 to 7 days, after the treatment of the plants with the active compounds.

The fact that the active compounds are well tolerated by plants in the concentrations necessary for controlling plant diseases makes possible treatment of above ground plant parts, of plant propagation material and seed, and of the soil.

In this connection, the active compounds according to the invention can be used particularly successfully in controlling cereal diseases, such as, e.g., *Puccinia* species, and diseases in viticulture and in the cultivation of fruit and vegetables, such as, e.g., *Botrytis, Venturia* or *Alternaria* species.

The active compounds according to the invention are also suitable for increasing the crop yield. In addition, they are of lower toxicity and are well tolerated by plants.

The active compounds according to the invention can also optionally be used, in specific concentrations and application amounts, as herbicides, for affecting plant growth and for controlling animal pests. They can optionally also be used as intermediates and precursors for the synthesis of additional active compounds.

All plants and plant parts can be treated according to the invention. In this connection, plants are to be understood as meaning all plants and plant populations, such as desirable and undesirable wild plants or cultivated plants (including naturally occurring cultivated plants). Cultivated plants can be plants which can be obtained by conventional breeding and optimization methods or by biotechnological and genetic engineering methods or combinations of these methods, including transgenic plants and including plant varieties which may or may not be protected by laws on variety certification. Plant parts should be understood as meaning all above ground and subsoil parts and organs of plants, such as shoot, leaf, flower and root, examples which are listed being leaves, needles, stalks, stems, flowers, fruiting bodies, fruits and seeds, and also roots, tubers and rhizomes. Plant parts also include harvested crops, and also vegetative and generative propagation material, for example cuttings, tubers, rhizomes, slips and seeds.

The treatment according to the invention of the plants and plant parts with the active compounds is carried out directly or by acting on the environment, habitat or storage area thereof using conventional treatment methods, e.g. by dipping, spraying, evaporating, atomizing, scattering, spreading and, with propagation material, in particular with seeds, furthermore by coating with one or more layers.

Mycotoxins

In addition, it is possible, by the treatment according to the invention, to reduce the mycotoxin content in harvested crops and the foodstuffs and feedstuffs prepared therefrom. In this connection, mention may in particular but not exclusively be made of the following mycotoxins: deoxynivalenol (DON), nivalenol, 15-Ac-DON, 3-Ac-DON, T2 and HT2 toxin, fumonisins, zearalenone, moniliformin, fusarin, diacetoxyscirpenol (DAS), beauvericin, enniatin, fusaroproliferin, fusarenol, ochratoxins, patulin, ergot alkaloids and aflatoxins, which can be caused, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, and others, and also by *Aspergillus* spec., *Penicillium* spec., *Claviceps purpurea, Stachybotrys* spec., and others.

Material Protection

In material protection, the substances according to the invention can be used for the protection of industrial materials from attack and destruction by undesirable microorganisms.

Industrial materials are to be understood in the present context as meaning nonliving materials which have been prepared for use in industry. For example, industrial materials which are to be protected by active compounds according to the invention from microbial change or destruction can be adhesives, sizes, paper and board, textiles, leather, wood, paints and plastic articles, cooling lubricants and other materials which can be attacked or destroyed by microorganisms. In the context of the materials to be protected, mention may also be made of parts of production plants, for example cooling water circuits, which can be detrimentally affected by proliferation of microorganisms. In the context of the present invention, mention may preferably be made, as industrial materials, of adhesives, sizes, papers and boards, leather, wood, paints, cooling lubricants and heat-transfer liquids, particularly preferably of wood.

Examples which may be mentioned of microorganisms which can decompose or modify industrial materials are bacteria, fungi, yeasts, algae and slime organisms. The active compounds according to the invention are preferably active against fungi, in particular molds, wood-discoloring and wood-destroying fungi (Basidiomycetes), and against slime organisms and algae.

Mention may be made, by way of example, of microorganisms of the following genera:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*,
*Staphylococcus*, such as *Staphylococcus aureus*.

Formulations

The present invention relates to a composition for controlling undesirable microorganisms, comprising at least one of the amidines according to the invention.

The amidines according to the invention can for this, depending on their respective physical and/or chemical properties, be converted into the standard formulations, such as solutions, emulsions, suspensions, powders, foams, pastes, granules, aerosols, very fine encapsulations in polymeric substances and in coating materials for seed, and also ULV coldand hot-fogging formulations.

These formulations are prepared in a known way, e.g. by mixing the active compounds with extenders, that is liquid solvents, liquefied gases under pressure and/or solid carriers, optionally with the use of surface-active agents, that is emulsifiers and/or dispersants and/or foaming agents. In the case of the use of water as extender, use may also be made, e.g., of organic solvents as cosolvents. Possible liquid solvents are essentially: aromatic hydrocarbons, such as xylene, toluene or alkylnaphthalenes, chlorinated aromatic hydrocarbons or chlorinated aliphatic hydrocarbons, such as chlorobenzenes, chloroethylenes or methylene chloride, aliphatic hydrocarbons, such as cyclohexane or paraffins, e.g. petroleum fractions, alcohols, such as butanol or glycol, and the ethers and esters thereof, ketones, such as acetone, methyl ethyl ketone, methyl isobutyl ketone or cyclohexanone, strongly polar solvents, such as dimethylformamide and dimethyl sulfoxide, and also water. Liquefied gaseous extenders or carriers are to be understood as meaning those liquids which are in the gas form at standard temperature and at standard pressure, e.g. aerosol propellants, such as halogenated hydrocarbons and also butane, propane, nitrogen and carbon dioxide. Possible solid carriers are, e.g., ground natural minerals, such as kaolins, argillaceous earths, talc, chalk, quartz, attapulgite, montmorillonite or diatomaceous earth, and ground synthetic minerals, such as highly dispersed silica, aluminum oxide and silicates. Possible solid carriers for granules are, e.g., broken and fractionated natural rocks, such as calcite, pumice, marble, sepiolite or dolomite, and also synthetic granules formed from inorganic and organic dusts, and also granules formed from organic material, such as sawdust, coconut shells, maize cobs and tobacco stalks. Possible emulsifiers and/or foaming agents are, e.g., nonionic and anionic emulsifiers, such as polyoxyethylene fatty acid esters, polyoxyethylene fatty alcohol ethers, e.g. alkylaryl polyglycol ethers, alkylsulfonates, alkyl sulfates, arylsulfonates, and also protein hydrolyzates. Possible dispersants are, e.g., lignosulfite waste liquors and methylcellulose.

Use may be made, in the formulations, of stickers, such as carboxymethylcellulose, natural and synthetic polymers in the powder, granule or latex form, such as gum arabic, polyvinyl alcohol, polyvinyl acetate, and also natural phospholipids, such as cephalins and lecithins, and synthetic phospholipids. Other possible additives are mineral and vegetable oils.

Use may also be made of colorants, such as inorganic pigments, e.g. iron oxide, titanium oxide, Prussian blue, and organic colorants, such as alizarin dyes, azo dyes and metal phthalocyanine dyes, and trace elements, such as salts of iron, manganese, boron, copper, cobalt, molybdenum and zinc.

The formulations generally comprise between 0.1 and 95% by weight of active compound, preferably between 0.5 and 90%.

The formulations described above can be used in a method according to the invention for controlling undesirable microorganisms, in which the amidines according to the invention are applied to the microorganisms and/or to the habitat thereof.

Seed Treatment

The controlling of phytopathogenic fungi by the treatment of the seed of plants has been known for a long time and is the subject matter of continuous improvements. Nevertheless, a series of problems arises in the treatment of seed, which problems may not always be satisfactorily solved. Thus, it is desirable to develop methods for protecting the seed and the germinating plant which render superfluous or at least markedly reduce the additional application of plant protection compositions after sowing or after emergence of the plants. It is furthermore desirable to optimize the amount of the active compound used, so that the seed and the germinating plant are given the best possible protection against attack by phytopathogenic fungi but without the plant itself being damaged by the active compound used. In particular, methods for the treatment of seed should also include the intrinsic fungicidal properties of transgenic plants in order to achieve optimum protection of the seed and the germinating plant with a minimum expenditure of plant protection compositions.

The present invention therefore also relates in particular to a method for the protection of seed and germinating plants from attack by phytopathogenic fungi, by treating the seed with a composition according to the invention.

The invention likewise relates to the use of the compositions according to the invention for the treatment of seed to protect the seed and the germinating plant from phytopathogenic fungi.

Furthermore, the invention relates to seed which has been treated with a composition according to the invention in order to protect from phytopathogenic fungi.

One of the advantages of the present invention is that, because of the particular systemic properties of the compositions according to the invention, the treatment of the seed with these compositions not only protects the seed itself from phytopathogenic fungi but also protects the plants resulting therefrom after emergence from phytopathogenic fungi. In this way, the immediate treatment of the crop at the time of sowing or shortly thereafter can be dispensed with.

It is likewise to be regarded as advantageous that the mixtures according to the invention can in particular also be used with transgenic seed.

The compositions according to the invention are suitable for the protection of seed of any plant variety used in agriculture, in the greenhouse, in forests or in horticulture. The seed concerned in this connection is in particular seed of cereals (such as wheat, barley, rye, millet and oats), maize, cotton, soya, rice, potatoes, sunflowers, beans, coffee, beet (e.g., sugarbeet and forage beet), peanuts, vegetables (such as tomatoes, cucumbers, onions and lettuce), lawns and ornamental plants. The treatment of the seed of cereals (such as wheat, barley, rye and oats), maize and rice is of particular importance.

In the context of the present invention, the composition according to the invention is applied to the seed alone or in a suitable formulation. Preferably, the seed is treated in a condition sufficiently stable for no damage to occur during the treatment. In general, the treatment of the seed can be carried out at any point in time between harvesting and sowing. Use is usually made of seed which has been separated from the plant and freed from pods, shells, stalks, skins, hairs or fruit flesh. Thus, it is possible, for example, to use seed which has been harvested, cleaned and dried up to a moisture content of less than 15% by weight. Alternatively, it is also possible to use seed which, after drying, has been treated, e.g. with water, and then dried again.

In general, care must be taken, in the treatment of the seed, that the amount of the composition according to the invention and/or of additional additives applied to the seed is chosen so that the germination of the seed is not impaired or that the plant resulting therefrom is not damaged. This is to be taken into consideration in particular with active compounds which may show phytotoxic effects at certain application rates.

The compositions according to the invention can be applied immediately, thus without comprising additional components and without having been diluted. It is generally preferable to apply the compositions to the seed in the form of a suitable formulation. Suitable formulations and methods for seed treatment are known to a person skilled in the art and are described, e.g., in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations which can be used according to the invention can be converted into the usual seed dressing formulations, such as solutions, emulsions, suspensions, powders, foams, slurries or other coating materials for seed, and also ULV formulations.

These formulations are prepared in a known way by mixing the active compounds or active compound combinations with conventional additives, such as, for example, conventional extenders and also solvents or diluents, colorants, wetting agents, dispersants, emulsifiers, antifoaming agents, preservatives, secondary thickeners, adhesives, gibberellins and also water.

Suitable colorants which may be present in the seed dressing formulations which can be used according to the invention comprise all colorants conventional for such purposes. In this connection, use may be made both of pigments, which are sparingly soluble in water, and dyes, which are soluble in water. Mention may be made, as examples, of the colorants known under the descriptions Rhodamine B, C.I. Pigment Red 112 and C.I. Solvent Red 1.

Possible wetting agents which can be present in the seed dressing formulations which can be used according to the invention comprise all substances which promote wetting and are conventional in the formulation of agrochemical active compounds. Use may preferably be made of alkylnaphthalenesulfonates, such as diisopropyl- or diisobutylnaphthalenesulfonates.

Suitable dispersants and/or emulsifiers which may be present in the seed dressing formulations which can be used according to the invention comprise all nonionic, anionic and cationic dispersants conventional in the formulation of agrochemical active compounds. Use may preferably be made of nonionic or anionic dispersants or mixtures of nonionic or anionic dispersants. Mention may in particular be made, as suitable nonionic dispersants, of ethylene oxide/propylene oxide block polymers, alkylphenol polyglycol ethers and also tristyrylphenol polyglycol ethers, and the phosphated or sulfated derivatives thereof. Suitable anionic dispersants are in particular lignosulfonates, polyacrylic acid salts and arylsulfonate/formaldehyde condensates.

Antifoaming agents which may be present in the seed dressing formulations which can be used according to the invention comprise all foam-inhibiting substances conventional in the formulation of agrochemical active compounds. Use may preferably be made of silicone defoaming agents and magnesium stearate.

Preservatives which may be present in the seed dressing formulations which can be used according to the invention comprise all substances which can be used in agrochemical compositions for such purposes. Mention may be made, by way of example, of dichlorophen and benzyl alcohol hemiformal.

Possible secondary thickeners which may be present in the seed dressing formulations which can be used according to the invention comprise all substances which can be used in agrochemical compositions for such purposes. Preferably suitable are cellulose derivatives, acrylic acid derivatives, xanthan, modified clays and highly dispersed silica.

Possible adhesives which may be present in the seed dressing formulations which can be used according to the invention comprise all conventional binders which can be used in seed dressings. Mention may preferably be made of polyvinylpyrrolidone, polyvinyl acetate, polyvinyl alcohol and tylose.

Possible gibberellins which may be present in the seed dressing formulations which can be used according to the invention preferably comprise gibberellins A1, A3 (=gibberellic acid), A4 and A7; use is particularly preferably made of gibberellic acid. Gibberellins are known (cf. R. Wegler, "Chemie der Pflanzenschutz-und Schädlingsbekämpfungsmittel" [Chemistry of Plant Protection and Pest Control Agents], Vol. 2, Springer Verlag, 1970, pp. 401-412).

The seed dressing formulations which can be used according to the invention can be used, either directly or after prior diluting with water, for the treatment of seed of the most varied species. Thus, the concentrates or the preparations which can be obtained therefrom by diluting with water can be used for the dressing of the seed of cereals, such as wheat, barley, rye, oats and triticale, and also the seed of maize, rice, rape, peas, beans, cotton, sunflowers and beet, or also of vegetable seed of the most varied natures. The seed dressing formulations which can be used according to the invention or the diluted preparations thereof can also be used for the dressing of seed of transgenic plants. In this connection, additional synergistic effects may also occur in interaction with the substances formed by expression.

All mixing devices which can be conventionally used for dressing are suitable for the treatment of seed with the seed dressing formulations which can be used according to the invention or the preparations prepared therefrom by addition of water. Specifically, the dressing procedure is such that the seed is introduced into a mixer, the amount of seed dressing formulation desired each time is added, either as such or after prior dilution with water, and mixing is carried out until the formulation is uniformly distributed over the seed. If appropriate, a drying operation follows.

The application rate of the seed dressing formulations which can be used according to the invention can be varied within a relatively wide range. It depends on the respective content of the active compounds in the formulations and on the seed. The application rates of active compound combination are generally between 0.001 and 50 g per kilogram of seed, preferably between 0.01 and 15 g per kilogram of seed.

Mixture with Known Fungicides, Bactericides, Acaricides, Nematicides or Insecticides The amidines according to the invention can be used, as such or in their formulations, also in a mixture with known fungicides, bactericides, acaricides, nematicides or insecticides, in order thus, e.g., to broaden the spectrum of activity or to prevent the development of resistance.

A mixture with other known active compounds, such as herbicides, or with fertilizers and growth regulators, safeners or semiochemicals is also possible.

In addition, the compounds of the formula (I) according to the invention also exhibit very good antimycotic activities. They have a very broad spectrum of antimycotic activity, in particular against dermatophytes and budding fungi, molds and diphasic fungi (e.g. against *Candida* species, such as *Candida albicans, Candida glabrata*), and also *Epidermophyton floccosum, Aspergillus* species, such as *Aspergillus niger* and *Aspergillus fumigatus, Trichophyton* species, such as *Trichophyton mentagrophytes, Microsporon* species, such as *Microsporon canis* and *audouinii*. The enumeration of these fungi does not represent in any way a limitation on the mycotic spectrum which can be included but has only an illustrative nature.

The 3-substituted phenoxyphenylamidines according to the invention can accordingly be used both in medicinal and in nonmedicinal applications.

The active compounds can be applied as such, in the form of their formulations or in the form of the application forms prepared therefrom, such as ready-to-use solutions, suspensions, sprayable powders, pastes, soluble powders, dusts and granules. Application takes place in standard fashion, e.g. by pouring, spraying, atomizing, scattering, dusting, foaming, spreading, and the like. It is furthermore possible to apply the active compounds by the ultra-low-volume method or to inject the active compound preparation or the active compound itself into the soil.

The seed of the plant can also be treated.

When the amidines according to the invention are used as fungicides, the application rates can be varied within a relatively wide range depending on the type of application. In the treatment of plant parts, the application rates of active compound are generally between 0.1 and 10 000 g/ha, preferably between 10 and 1000 g/ha. In seed treatment, the application rates of active compound are generally between 0.001 and 50 g per kilogram of seed, preferably between 0.01 and 10 g per kilogram of seed. In soil treatment, the application rates of active compound are generally between 0.1 and 10 000 g/ha, preferably between 1 and 5000 g/ha.

GMOs

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or hypoochondrial genome gives the transformed plant new or improved agronomic or other properties by expressing a protein or polypeptide of interest or by downregulating or silencing other gene(s) which are present in the plant (using, for example, antisense technology, cosuppression technology or RNA interference—RNAi technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are suitable for mobilizing the defense system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably treated according to the invention include all plants which have genetic material which imparts particularly advantageous, useful traits to these plants (whether obtained by breeding and/or biotechnological means).

Plants and plant cultivars which are also preferably treated according to the invention are resistant against one or more biotic stresses, i.e. the said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention are those plants characterized by enhanced yield characteristics. Increased yield in the said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants that contain the genetic determinants responsible for male sterility is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male sterile plants can also be obtained by plant biotechnology methods, such as genetic engineering. A particularly useful means of obtaining male-sterile plants is described in WO 89/10396 in which, for example, a ribonuclease, such as a barnase, is selectively expressed in the tapetum cells in the stamens. Fertility can then be restored by expression in the tapetum cells of a ribonuclease inhibitor, such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an *eleusine* EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226.

Other herbicide-resistant plants are for example plants that are made tolerant to herbicides inhibiting the enzyme glutamine synthase, such as bialaphos, phosphinotricin or glufosinate. Such plants can be obtained by expressing an enzyme detoxifying the herbicide or a mutant of the glutamine synthase enzyme that is resistant to inhibition. One such efficient detoxifying enzyme is an enzyme encoding a phosphinotricin acetyltransferase (such as the bar or pat protein from *Streptomyces* species). Plants expressing an exogenous phosphinotricin acetyltransferase are for example described in U.S. Pat. No. 5,561,236; U.S. Pat. No. 5,648, 477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112, 665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentizate. Plants tolerant to HPPD inhibitors can be transformed with a gene encoding a naturally occurring resistant HPPD enzyme, or a gene encoding a mutated HPPD enzyme as described in WO 1996/038567, WO 1999/024585 and WO 1999/024586. Tolerance to HPPD inhibitors can also be obtained by transforming plants with genes encoding certain enzymes enabling the formation of homogentizate despite the inhibition of the native HPPD enzyme by the HPPD inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Further herbicide-resistant plants are plants that are made tolerant to acetolactate synthase (ALS) inhibitors. Known ALS inhibitors include, for example, sulfonylurea, imidazolinone, triazolopyrimidines, pyrimidinyloxy(thio)benzoates and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also in U.S. Pat. No. 5,605,011, U.S. Pat. No. 5,378,824, U.S. Pat. No. 5,141,870 and U.S. Pat. No. 5,013, 659. The production of sulfonylurea-tolerant plants and imidazolinone-tolerant plants is described in U.S. Pat. No. 5,605, 011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and in international publication WO 1996/033270. Other imidazolinone-tolerant plants are also described in, for example, WO 2004/040012, WO 2004/106529, WO 2005/020673, WO 2005/093093, WO 2006/007373, WO 2006/015376, WO 2006/024351 and WO 2006/060634. Further sulfonylurea- and imidazolinone-tolerant plants are also described in, for example, WO 2007/024782.

Other plants tolerant to imidazolinone and/or sulfonylurea can be obtained by induced mutagenesis, selection in cell cultures in the presence of the herbicide or by mutation breeding as described for example for soybeans in U.S. Pat. No. 5,084,082, for rice in WO 1997/41218, for sugarbeet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g. proteins of the Cry protein classes Cry1Ab, Cry1Ac, Cry1F, Cry2Ab, Cry3Ae or Cry3Bb or insecticidal portions thereof, or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by maize event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604;

5) an insecticidal secreted protein from *Bacillus thuringiensis* or *Bacillus cereus*, or an insecticidal portion thereof, such as the vegetative insecticidal (VIP) proteins listed at http://www.lifesci.sussex.ac.uk/Home/Neil_Crickmore/Bt/vip.html, e.g., proteins from VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795);

7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose) polymerase (PARP) gene in the plant cells or plants as described in WO 2000/004173 or EP 04077984.5 or EP 06009836.5;

b. plants which contain a stress tolerance enhancing transgene capable of reducing the expression and/or activity of the PARG encoding genes of the plants or plant cells, as described e.g. in WO 2004/090140;

c. plants which contain a stress tolerance enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, e.g., in EP 04077624.7 or WO 2006/133827 or PCT/EP07/002,433.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behavior, the gelling strength, the starch grain size and/or the starch grain morphology, is changed in comparison with the synthesized starch in wild type plant cells or plants, so that this modified starch is better suited for special applications. The said transgenic plants synthesizing a modified starch are disclosed, for example, in EP 0 571 427, WO 1995/004826, EP 0 719 338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026 or WO 1997/20936.

2) transgenic plants which synthesize nonstarch carbohydrate polymers or which synthesize nonstarch carbohydrate polymers with altered properties in comparison to wild type plants without genetic modification. Examples are plants producing polyfructose, especially of the inulin and levan type, as disclosed in EP 0 663 956, WO 1996/001904, WO 1996/021023, WO 1998/039460 and WO 1999/024593, plants producing alpha-1,4-glucans as disclosed in WO 1995/031553, US 2002/031826, U.S. Pat. No. 6,284,479, U.S. Pat. No. 5,712,107, WO 1997/047806, WO 1997/047807, WO 1997/047808 and WO 2000/14249, plants producing alpha-1,6 branched alpha-1,4-glucans, as disclosed in WO 2000/73422, and plants producing alternan, as disclosed in WO 2000/047727, EP 06077301.7, U.S. Pat. No. 5,908,975 and EP 0 728 213.

3) transgenic plants which produce hyaluronan, as for example disclosed in WO 2006/032538, WO 2007/039314, WO 2007/039315, WO 2007/039316, JP 2006/304779 and WO 2005/012529.

Plants or plant cultivars (obtained by plant biotechnology methods, such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, containing an altered form of cellulose synthase genes as described in WO 1998/000549, b) plants, such as cotton plants, containing an altered form of rsw2 or rsw3 homologous nucleic acids as described in WO 2004/053219;

c) plants, such as cotton plants, with increased expression of sucrose phosphate synthase as described in WO 2001/017333;

d) plants, such as cotton plants, with increased expression of sucrose synthase as described in WO 02/45485;

e) plants, such as cotton plants, wherein the timing of the plasmodesmatal gating at the basis of the fiber cell is altered, e.g. through downregulation of fiber selective β-1,3-glucanase as described in WO 2005/017157;

f) plants, such as cotton plants, having fibers with altered reactivity, e.g. through the expression of the N-acetylglucosamine transferase gene including nodC and chitin synthase genes as described in WO 2006/136351.

Plants or plant cultivars (obtained by plant biotechnology methods, such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, producing oil having a high oleic acid content as described, e.g., in U.S. Pat. No. 5,969,169, U.S. Pat. No. 5,840,946, U.S. Pat. No. 6,323,392 or U.S. Pat. No. 6,063,947;

b) plants such as oilseed rape plants, producing oil having a low linolenic acid content as described in U.S. Pat. No. 6,270,828, U.S. Pat. No. 6,169,190 or U.S. Pat. No. 5,965,755;

c) plants such as oilseed rape plants, producing oil having a low level of saturated fatty acids as described, e.g., in U.S. Pat. No. 5,434,283.

Particularly useful transgenic plants which may be treated according to the invention are plants which comprise one or more genes which encode one or more toxins, are the transgenic plants which are sold under the following trade names: YIELD GARD® (for example maize, cotton, soybeans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soybean varieties which are sold under the following trade names: Roundup Ready® (tolerance to glyphosate, for example maize, cotton, soybean), Liberty Link® (tolerance to phosphinotricin, for example oilseed rape), IMI® (tolerance to imidazolinone) and SCS® (tolerance to sulfonylurea), for example maize. Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases from various national or regional regulatory agencies (see for example http://gmoinfojrc.it/gmp_browse.aspx and http://www.agbios.com/dbase.php).

The preparation and the use of the active compounds according to the invention is intended to be more fully explained from the following examples without, however, being limited to these.

PREPARATION EXAMPLES

Example 1

N-Ethyl-N-methyl-N'-[4-(isopropoxyiminomethyl)-2,5-dimethylphenyl]form-amidine 0.29 g (1.38 mmol) of 4-(isopropoxyiminomethyl)-2,5-dimethylaniline is dissolved in 10 ml of toluene, and 0.3 ml of a solution of N-ethyl-N-methylformamidine dimethyl acetal in methanol (60%) is added. The reaction mixture is stirred at 50° C. for 12 h, freed from the solvent under reduced pressure and purified by column chromatography. This gives 0.38 g of product (purity 90.0%, yield 95.0%; log P (pH2.3)=1.76).

Synthesis of the Starting Materials 4-(Isopropoxyiminomethyl)-2,5-dimethylaniline 0.32 g (2.10 mmol) of 4-amino-2,5-dimethylbenzaldehyde is initially charged in 10 ml of methanol, 0.31 g (2.73 mmol) of O-isopropyl hydroxylamine hydrochloride is added at room temperature and the reaction mixture is heated under reflux for 6 h. The mixture is then concentrated using a rotary evaporator, the residue is taken up in dichloromethane, extracted twice with water, dried over $Na_2SO_4$ and freed from the solvent under reduced pressure. This gives 0.35 g of product (purity 98.0%, yield 79.1%, log P (pH 2.3)=2.77).

4-Amino-2,5-dimethylbenzaldehyde 6.06 g (50.0 mmol) of 2,5-dimethylaniline are initially charged in 1000 ml of DMSO, 13.55 g (100.0 mmol) of copper(II) chloride are added and concentrated hydrochloric acid is then added slowly. The reaction mixture is heated at 90° C. for 3 h and then added to ice-water. After addition of aqueous sodium hydroxide solution, the mixture is filtered and extracted repeatedly with ethyl acetate, and the combined organic phases are dried over $Na_2SO_4$ and freed from solvent under reduced pressure. The crude product is purified by column chromatography. (2.27 g, purity 75.0%, yield 22.8%, log P (pH 2.3)=1.34).

Example 2

N-Ethyl-N-methyl-N'-[4-(benzyloxyiminomethyl)-2,5-dimethylphenyl]form-amidine 0.34 g (1.10 mmol) of 4-(benzyloxyiminomethyl)-2,5-dimethylaniline is dissolved in 10 ml of toluene, and 0.3 ml of a solution of N-ethyl-N-methylformamidine dimethylacetal in methanol (60%) is added. The reaction mixture is stirred at 50° C. for 12 h, freed from the solvent under reduced pressure and purified by column chromatography. This gives 0.15 g of product (purity 80.0%, yield 33.4%; log P (pH2.3)=2.02).

Synthesis of the Starting Material 4-(Benzyloxyiminomethyl)-2,5-dimethylaniline 0.50 g (2.51 mmol) of 4-amino-2,5-dimethylbenzaldehyde is initially charged in 10 ml of methanol, 0.40 g (3.27 mmol) of O-benzyl hydroxylamine hydrochloride is added at room temperature and the reaction mixture is heated under reflux for 18 h. The mixture is then concentrated using a rotary evaporator and the residue is taken up in dichloromethane, extracted twice with water, dried over $Na_2SO_4$ and freed from the solvent under reduced pressure. This gives 0.3.8 g of product (purity 82.0%, yield 47.7%, log P (pH 2.3)=4.22).

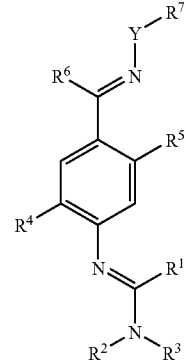

(I)

TABLE II

| No. | logP neutral | logP acidic | Y | $R^1$ | $R^2$ | $R^3$ | $R^4$ | $R^5$ | $R^6$ | $R^7$ |
|---|---|---|---|---|---|---|---|---|---|---|
| 1 | | | O | H | Me | Me | Me | Me | H | 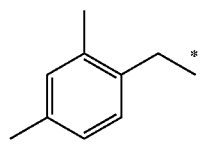 |

TABLE II-continued
| No. | logP neutral | logP acidic | Y | R¹ | R² | R³ | R⁴ | R⁵ | R⁶ | R⁷ |
|---|---|---|---|---|---|---|---|---|---|---|
| 2 | | | O | H | Me | Me | Me | Me | H | 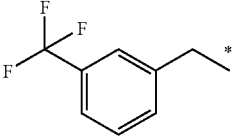 |
| 3 | | | O | H | Et | Me | Me | Me | H | 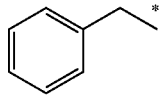 |
| 4 | 4.71 | 2.02 | O | H | Et | Me | Me | Me | H | 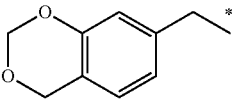 |
| 5 | | | O | H | Et | Me | Me | Me | H | 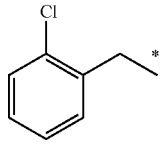 |
| 6 | | | O | H | Et | Me | Me | Me | H | 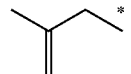 |
| 7 | | | O | H | Et | Me | Me | Me | H | 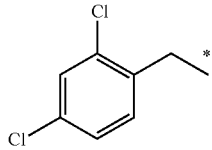 |
| 8 | | | O | H | Et | Me | Me | Me | H | 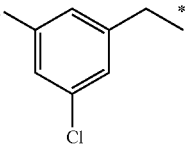 |
| 9 | 5.17 | 2.19 | O | H | Et | Me | Me | Me | Me |  |
| 10 | 4.42 | 1.92 | O | H | Et | Me | Me | Me | Me |  |
| 11 | | 2.21 | O | H | Et | Me | Me | Me | Me | 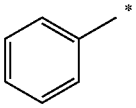 |
| 12 | 6.26 | 3.05 | O | H | Et | Me | Me | Me | Me | 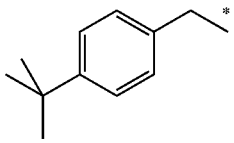 |
| 13 | 4.98 | 2.22 | O | H | Et | Me | Me | Me | Me | 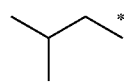 |

TABLE II-continued
| No. | logP neutral | logP acidic | Y | R¹ | R² | R³ | R⁴ | R⁵ | R⁶ | R⁷ |
|---|---|---|---|---|---|---|---|---|---|---|
| 14 | 5.24 | 2.20 | O | H | Et | Me | Me | Me | Me | 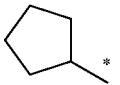 |
| 15 | 4.00 | 1.80 | O | H | Et | Me | Me | Me | Me | 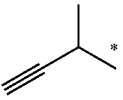 |
| 16 | 3.91 | 1.72 | O | H | Et | Me | Me | Me | Me | 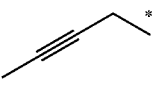 |
| 17 | 4.24 | 1.88 | O | H | Et | Me | Me | Me | Me | 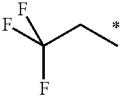 |
| 18 | 3.05 | 1.43 | O | H | Et | Me | Me | Me | Me | 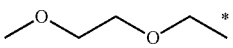 |
| 19 | 5.20 | 2.32 | O | H | Et | Me | Me | Me | Me | 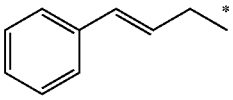 |
| 20 | 5.33 | 2.38 | O | H | Et | Me | Me | Me | Me | 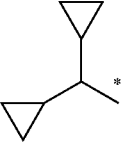 |
| 21 | 5.10 | 2.30 | O | H | Et | Me | Me | Me | Me | 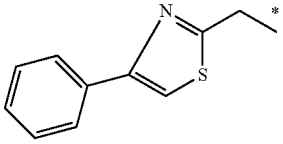 |
| 22 | 5.77 | 2.69 | O | H | Et | Me | Me | Me | Me | 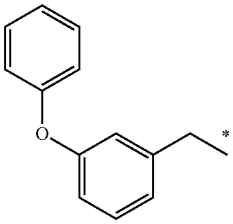 |
| 23 | 3.86 | 1.60 | O | H | Et | Me | Me | Me | Me | 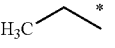 |
| 24 | 3.33 | 1.38 | O | H | Et | Me | Me | Me | Me |  |
| 25 | 5.55 | 2.56 | O | H | Et | Me | Me | Me | Me | 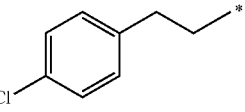 |
| 26 | 3.10 | 2.15 | O | H | Et | Me | Me | Me | Me | 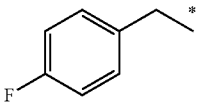 |

TABLE II-continued
| No. | logP neutral | logP acidic | Y | R¹ | R² | R³ | R⁴ | R⁵ | R⁶ | R⁷ |
|---|---|---|---|---|---|---|---|---|---|---|
| 27 | 5.09 | 2.39 | O | H | Et | Me | Me | Me | Me | 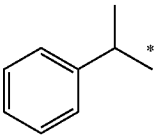 |
| 28 | 3.81 | 1.14 | O | H | Et | Me | Me | Me | Me | 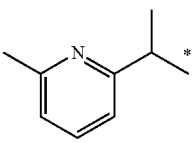 |
| 29 | 5.51 | 3.75 | O | H | Et | Me | Me | Me | Me | 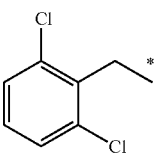 |
| 30 | 5.79 | 2.71 | O | H | Et | Me | Me | Me | Me | 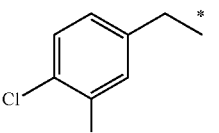 |
| 31 | 4.65 | 2.07 | O | H | Et | Me | Me | Me | Me | 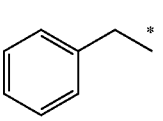 |
| 32 | 3.95 | 1.67 | O | H | Et | Me | Me | Me | Me | 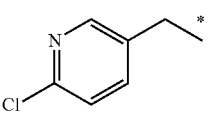 |
| 33 | 4.86 | 2.24 | O | H | Et | Me | Me | Me | Me | 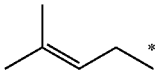 |
| 34 | 5.28 | 2.59 | O | H | Et | Me | Me | Me | Me | 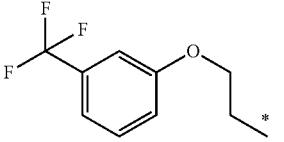 |
| 35 | 4.02 | 1.72 | O | H | Et | Me | Me | Me | Me | 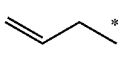 |
| 36 | 3.63 | 1.68 | O | H | Et | Me | Me | Me | Me | 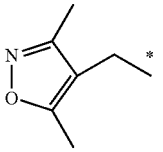 |
| 37 | 4.43 | 1.90 | O | H | Et | Me | Me | Me | Me | 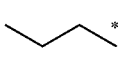 |
| 38 | 5.67 | 2.46 | O | H | Et | Me | Me | Me | Me | 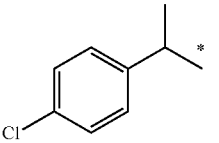 |

TABLE II-continued

| No. | logP neutral | logP acidic | Y | R¹ | R² | R³ | R⁴ | R⁵ | R⁶ | R⁷ |
|---|---|---|---|---|---|---|---|---|---|---|
| 39 | 4.98 | 2.11 | O | H | Et | Me | Me | Me | H |  |
| 40 | 4.41 | 1.76 | O | H | Et | Me | Me | Me | H |  |
| 41 | 6.01 | 2.56 | O | H | Et | Me | Me | Me | H | 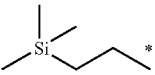 |
| 42 | 6.12 | 2.66 | O | H | Et | Me | Me | Me | H | 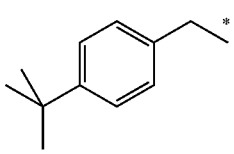 |
| 43 | 5.23 | 2.43 | O | H | Et | Me | Me | Me | H | 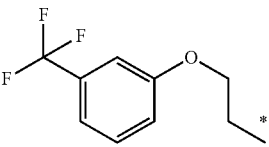 |
| 44 | 6.21 | 2.76 | O | H | Et | Me | Me | Me | Me | 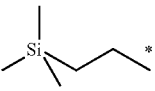 |
| 45 |  | 1.91 | NH | H | Et | Me | Me | Me | Me | 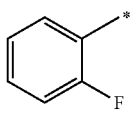 |
| 46 | 4.75 | 1.79 | CH₂ | H | Et | Me | Me | Me | Me | 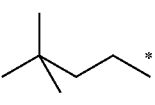 |
| 47 | 3.95 | 1.67 | O | H | Et | Me | Me | Me | H | 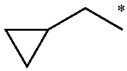 |
| 48 | 5.89 | 2.30 | O | H | Et | Me | Me | Me | H | 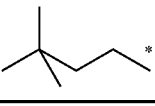 |

Use Examples

*Alternaria* Test (Tomato)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are inoculated with an aqueous spore suspension of *Alternaria solani*. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

In this test, the compounds 3, 20, 41 and 42 according to the invention of Table II above show, at an active compound concentration of 100 ppm, an efficacy of 70% or more.

*Uromyces* Test (Bean)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are inoculated with an aqueous spore suspension of the bean rust pathogen *Uromyces appendiculatus* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

In this test, the compounds 3, 20, 25, 41 and 42 according to the invention of Table II above show, at an active compound concentration of 100 ppm, an efficacy of 70% or more.

*Sphaerotheca* Test (Cucumber)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young cucumber plants are sprayed with the active compound preparation at the stated application rate. 1 day after the treatment, the plants are inoculated with a spore suspension of *Sphaerotheca fuliginea*. The plants are then placed in a greenhouse at 70% relative atmospheric humidity and a temperature of 23° C.

Evaluation is carried out 7 days after the inoculation. 0% means an efficacy which corresponds to that of the control, whereas an efficacy of 100% means that no infection is observed.

In this test, the compounds 3, 11, 12, 14, 15, 16, 17, 20, 21, 22, 25, 26, 29, 30, 31, 32, 33, 34, 36, 37, 39, 40, 41, 42 and 43 according to the invention of Table II above show, at an active compound concentration of 500 ppm, an efficacy of 70% or more.

*Erysiphe* Test (Barley)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are dusted with spores of *Erysiphe graminis* f.sp. hordei. The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

In this test, the compounds 3, 20, 25, 38 and 39 according to the invention of Table II above show, at an active compound concentration of 1000 ppm, an efficacy of 70% or more.

*Puccinia* Test (Wheat)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate. After the spray coating has dried on, the plants are sprayed with a conidia suspension of *Puccinia recondita*. The plants remain in an incubation cabin at 20° C. and 100% relative atmospheric humidity for 48 hours. The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

In this test, the compounds 3, 20, 25, 38 and 39 according to the invention of Table II above show, at an active compound concentration of 1000 ppm, an efficacy of 70% or more.

The invention claimed is:
1. A substituted phenylamidine of the formula (I)

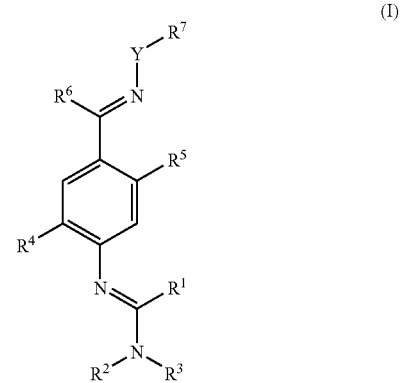

in which
Y is O;
$R^1$ is selected from the group consisting of hydrogen, methyl, and ethyl;
$R^2$ is methyl or ethyl;
$R^3$ is methyl or cyclopropyl;
or where
$R^2$ and $R^3$ together with the nitrogen atom to which they are attached form a piperidyl or pyrrolidyl radical;
$R^4$ and $R^5$ independently of one another are selected from the group consisting of Cl and F atoms and —$CF_3$, —$CF_2H$ and methyl groups;
$R^6$ is, independently of $R^7$, selected from the group consisting of hydrogen, methyl, and ethyl;
$R^7$ is selected from groups (i) to (iii) below:
(i) $C_{5-18}$-aryl or $C_{7-19}$-alkaryl groups of the formulae (II-f) to (II-j),

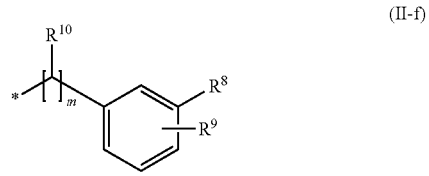

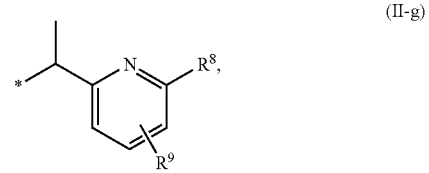

(II-h)

(II-i)

(II-j)

in which
m represents 0 or 1,
R⁸ is selected from the group consisting of hydrogen, chlorine, fluorine, bromine; methyl, trifluoromethyl, t-butyl and phenoxy;
R⁹ is selected from the group consisting of hydrogen, chlorine, fluorine, bromine; methyl, trifluoromethyl, t-butyl and phenoxy;
or in which R⁸ and R⁹ together with the atoms to which they are attached and, if appropriate, with further atoms selected from the group consisting of N, O and S may form a five- or six-membered ring;
R¹⁰ is selected from the group consisting of hydrogen and methyl;
  (ii) 2-(trimethylsilyl)ethyl, ethyl, allyl, n-propyl, 3-methylbut-2-en-1-yl, but-2-ynyl, 3-phenylprop-2-en-1-yl, 2-methylethoxy)methyl, cyclopentyl, 1-methylprop-2-yn-1-yl and 2-methylprop-2-en-1-yl
  (iii) radicals of the formula (III)

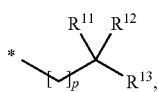

(III)

in which
p is 0 or 1,
R¹¹ is, independently of R¹² and R¹³, selected from the group consisting of hydrogen, methyl, ethyl, cyclopropyl and triflouromethyl;
R¹² is, independently of R¹⁰ and R¹³, selected from the group consisting of hydrogen, methyl, ethyl, cyclopropyl and triflouromethyl;
R¹³ is, independently of R¹¹ and R¹², selected from the group consisting of hydrogen, methyl, ethyl, cyclopropyl and triflouromethyl;
or a salt thereof.

2. A substituted phenylamidine selected from the group consisting of N'-{4-[(E)-{[(2,4-dimethylbenzyl)oxy]imino}methyl]-2,5-dimethylphenyl}-N,N-dimethylimidoformamide (1), N'-{2,5-dimethyl-4-[(E)-({[3-(trifluoromethyl)benzyl]oxy}imino)methyl]phenyl}-N,N-dimethylimidoformamide (2), N'-(4-{(E)-[(benzyloxy)imino]methyl}-2,5-di-methylphenyl)-N-ethyl-N-methylimidoformamide (3), N'-(4-{(E)-[(4H-1,3-benzodioxin-7-ylmethoxy)imino]methyl}-2,5-dimethylphenyl)-N-ethyl-N-methylimidoformamide (4), N'-{4-[(E)-{[(2-chlorobenzyl)oxy]imino}methyl]-2,5-dimethylphenyl}-N-ethyl-N-methylimidoformamide (5), N'-{2,5-dimethyl-4-[(E)-{[(2-methylprop-2-en-1-yl)oxy]imino}methyl]phenyl}-N-ethyl-N-methylimidoformamide (6), N'-{4-[(E)-{[(2,4-dichlorobenzyl)oxy]imino}methyl]-2,5-dimethylphenyl}-N-ethyl-N-methyl-imidoformamide (7), N'-{4-[(E)-{[(3,5-dichlorobenzyl)oxy]imino}methyl]-2,5-dimethyl-phenyl}-N-ethyl-N-methylimidoformamide (8), N-ethyl-N'-{4-[(1E)-N-tert-butoxyethanimidoyl]-2,5-dimethylphenyl}-N-methylimidoformamide (9), N-ethyl-N'-{4-[(1E)-N-isopropoxyethanimidoyl]-2,5-dimethylphenyl}-N-methylimidoformamide (10), N'-{2,5-dimethyl-4-[(1E)-N-phenoxyethanimidoyl]phenyl}-N-ethyl-N-methyl-imidoformamide (11), N'-(4-{(1E)-N-[(4-tert-butylbenzyl)oxy]ethanimidoyl}-2,5-dimethylphenyl)-N-ethyl-N-methylimidoformamide (12), N-ethyl-N'-{4-[(1E)-N-isobutoxyethanimidoyl]-2,5-dimethylphenyl}-N-methylimidoformamide (13), N'-{4-[(1E)-N-(cyclopentyloxy)ethanimidoyl]-2,5-dimethylphenyl}-N-ethyl-N-methylimidoformamide (14), N'-(2,5-dimethyl-4-{(1E)-N-[(1-methylprop-2-yn-1-yl)oxy]ethanimidoyl}phenyl)-N-ethyl-N-methylimidoformamide (15), N'-{4-[(1E)-N-(but-2-yn-1-yloxy)ethanimidoyl]-2,5-dimethylphenyl}-N-ethyl-N-methylimidoformamide (16), N'-{2,5-dimethyl-4-[(1E)-N-(2,2,2-trifluoroethoxy)ethanimidoyl]phenyl}-N-ethyl-N-methylimidoformamide (17), N'-{2,5-dimethyl-4-[(1E)-1-methyl-3,5,8-trioxa-2-azanon-1-en-1-yl]phenyl}-N-ethyl-N-methylimidoformamide (18), N'-{2,5-dimethyl-4-[(1E)-N-{[(2E)-3-phenylprop-2-en-1-yl]oxy}ethanimidoyl]phenyl}-N-ethyl-N-methylimidoformamide (19), N'-{4-[(1E)-N-(dicyclopropylmethoxy)ethanimidoyl]-2,5-dimethylphenyl}-N-ethyl-N-methyl-imidoformamide (20), N'-(2,5-dimethyl-4-{(1E)-N-[(4-phenyl-1,3-thiazol-2-yl)meth-oxy]ethanimidoyl}phenyl)-N-ethyl-N-methylimidoformamide (21), N'-(2,5-dimethyl-4-{(1E)-N-[(3-phenoxybenzyl)oxy]ethanimidoyl}phenyl)-N-ethyl-N-methylimidoformamide (22), N-ethyl-N'-{4-[(1E)-N-ethoxyethanimidoyl]-2,5-dimethylphenyl}-N-methylimidoformamide (23), N-ethyl-N'-{4-[(1E)-N-methoxyethanimidoyl]-2,5-dimethylphenyl}-N-methylimidoformamide (24), N'-(4-{(1E)-N-[2-(4-chlorophenyl)-ethoxy]ethanimidoyl}-2,5-dimethylphenyl)-N-ethyl-N-methylimidoformamide (25), N-ethyl-N'-{4-[(E)-{[(4-fluorobenzyl)oxy]ethanimidoyl]-2,5-dimethylphenyl}-N-methylimidoformamide (26), N'-(2,5-dimethyl-4-{(E)-[1-phenylethoxy]ethanimidoyl}-phenyl)-N-ethyl-N-methylimidoformamide (27), N'-(2,5-dimethyl-4-{(1E)-N-[1-(6-methylpyridin-2-yl)ethoxy]ethanimidoyl}phenyl)-N-ethyl-N-methylimidoformamide (28), N'-(4-{(1E)-N-[(2,6-dichlorobenzyl)oxy]ethanimidoyl}-2,5-dimethylphenyl)-N-ethyl-N-methylimidoformamide (29), N'-(4-{(1E)-N-[(3,4-dichlorobenzyl)oxy]-ethanimidoyl}-2,5-dimethylphenyl)-N-ethyl-N-methylimidoformamide (30), N'-(4-{(1E)-N-[benzyloxy]ethanimidoyl}-2,5-dimethylphenyl)-N-ethyl-N-methylimidoformamide (31), N'-(4-{(1E)-N-[(6-chloropyridin-3-yl)methoxy]ethanimidoyl}-2,5-dimethylphenyl)-N-ethyl-N-methylimidoformamide (32), N'-(2,5-dimethyl-4-{(1E)-N-[(3-methylbut-2-en-1-yl)oxy]ethanimidoyl}phenyl)-N-ethyl-N-methylimidoformamide (33), N'-{2,5-dimethyl-4-[(1E)-N-{2-[3-(trifluoromethyl)phenoxy]ethoxy}ethanimidoyl]phenyl}-N-ethyl-N-methylimidoformamide (34), N'-{4-[(1E)-N-(allyloxy)ethanimidoyl]-2,5-dimethylphenyl}-N-ethyl-N-methylimidoformamide (35), N'-(4-{(1E)-N-[(3,5- dimethylisoxazol-4-yl)methoxy]ethanimidoyl}-2,5-dimethylphenyl)-N-ethyl-N-methylimidoformamide (36), N'-{4-[(1E)-N-(n-propoxy)ethanimidoyl]-2,5-dimethylphenyl}-N-ethyl-N-methylimidoformamide (37), N'-(4-{(1E)-N-[1-(4-chloro-phenyl)ethoxy]ethanimidoyl}-2,5-dimethylphenyl)-N-ethyl-N-methylimidoformamide (38), N'-{4-[(E)-(tert-butoxyimino)methyl]-2,5-dimethylphenyl}-N-ethyl-N-methyl-imidoformamide (39), N-ethyl-N'-{4-[(E)-(isopropoxyimino)methyl]-2,5-dimethyl-phenyl}-N-methylimidoformamide (40), N'-(2,5-dimethyl-4-{(1E)-N-[2-(trimethylsilyl)-ethoxy]ethanimidoyl}phenyl)-N-ethyl-N-methylimidoformamide (41), N'-(4-{(E)-[(4-tert-butylphenoxy)imino]methyl}-2,5-dimethylphenyl)-N-ethyl-N-methylimidoformamide (42), N'-{2,5-dimethyl-4-[(1E)-N-{2-[3-(trifluoromethyl)phenoxy]ethoxy}-ethanimidoyl]phenyl}-N-ethyl-N-methylimidoformamide (43), N'-(2,5-dimethyl-4-{(1E)-N-[2-(trimethylsilyl)ethoxy]ethanimidoyl}phenyl)-N-ethyl-N-methylimidoformamide (44) N'-(4-{(E)-[(cyclopropylmethoxy)imino]methyl}-2,5-dimethylphenyl)-N-ethyl-N-methylimidoformamide (47), and N'-(4-{(E)-[(3,3-dimethylbutoxy)imino]methyl}-2,5-dimethylphenyl)-N-ethyl-N-methylimidoformamide (48).

3. The substituted phenylamidine as claimed in claim 1, which is selected from the group consisting of N'-(4-{(E)-[(benzyloxy)imino]methyl}-2,5-dimethylphenyl)-N-ethyl-N-methylimidoformamide (3), N'-{2,5-dimethyl-4-[(1E)-N-phenoxyethanimidoyl]phenyl}-N-ethyl-N-methylimidoformamide (11), and N-ethyl-N'-{4-[(E)-{[(4-fluorobenzyl)oxy]ethanimidoyl]-2,5-dimethylphenyl}-N-methylimidoformamide (26).

4. The substituted phenylamidine as claimed in claim 1, wherein $R^7$ is selected from groups (i) to (iii) below:

(i) $C_{5-18}$-aryl or $C_{7-19}$-alkaryl group of the formulae (II-f)

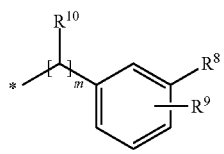

in which m represents 0 or 1, $R^8$ is selected from the group consisting of hydrogen, chlorine, fluorine, bromine; methyl, trifluoromethyl, t-butyl and phenoxy;

$R^9$ is selected from the group consisting of hydrogen, chlorine, fluorine, bromine; methyl, trifluoromethyl, t-butyl and phenoxy;

or in which $R^8$ and $R^9$ together with the atoms to which they are attached and, if appropriate, with further atoms selected from the group consisting of N, O and S may form a five- or six-membered ring;

$R^{10}$ is selected from the group consisting of hydrogen and methyl;

(ii) 2-(trimethylsilyl)ethyl, ethyl, allyl, n-propyl, 3-methylbut-2-en-1-yl, but-2-ynyl, 3-phenylprop-2-en-1-yl, 2-methylethoxy)methyl, cyclopentyl, 1-methylprop-2-yn-1-yl and 2-methylprop-2-en-1-yl (iii) radicals of the formula (III)

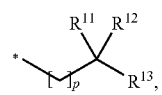

in which p is 0 or 1, $R^{11}$ is, independently of $R^{12}$ and $R^{13}$, selected from the group consisting of hydrogen, methyl, ethyl, cyclopropyl and trifluoromethyl;

$R^{12}$ is, independently of $R^{10}$ and $R^{13}$, selected from the group consisting of hydrogen, methyl, ethyl, cyclopropyl and trifluoromethyl;

$R^{13}$ is, independently of $R^{11}$ and $R^{12}$, selected from the group consisting of hydrogen, methyl, ethyl, cyclopropyl and trifluoromethyl;

or a salt thereof.

5. The substituted phenylamidine as claimed in claim 1, wherein $R^7$ is a (i) $C_{5-18}$-aryl or $C_{7-19}$-alkaryl group of the formulae (II-f)

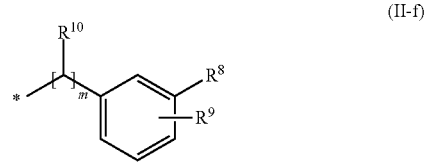

in which m represents 0 or 1, $R^8$ is selected from the group consisting of hydrogen, chlorine, fluorine, bromine; methyl, trifluoromethyl, t-butyl and phenoxy;

$R^9$ is selected from the group consisting of hydrogen, chlorine, fluorine, bromine; methyl, trifluoromethyl, t-butyl and phenoxy;

or in which $R^8$ and $R^9$ together with the atoms to which they are attached and, if appropriate, with further atoms selected from the group consisting of N, O and S may form a five- or six-membered ring; and $R^{10}$ is selected from the group consisting of hydrogen and methyl.

6. A composition for controlling phytopathogenic fungi, comprising at least one substituted phenylamidine as claimed in claim 1.

7. A composition for controlling phytopathogenic fungi, comprising at least one substituted phenylamidine as claimed in claim 2.

8. Seed treated with at least one substituted phenylamidine and/or salt thereof as claimed in claim 1.

9. A method for controlling phytopathogenic fungi, comprising applying a substituted phenylamidine and/or a salt thereof as claimed in claim 1 to the microorganisms and/or a habitat thereof.

10. A method for treating seed comprising treating seed with a substituted phenylamidine and/or a salt thereof according to claim 1.

11. A method for treating transgenic plants comprising treating a transgenic plant with a substituted phenylamidine and/or a salt thereof according to claim 1.

12. A method of claim 10, wherein said seed is seed of transgenic plants.

13. A method for protecting seed against phytopathogenic fungi by using seed treated with at least one substituted phenylamidine as claimed in claim 1.

14. A process for preparing a substituted phenylamidine as claimed in claim 1 which comprises at least one of the following steps (a) to (f):

(a) reaction of nitrobenzaldehydes or nitrobenzoketones of the formula (IV) with amines of the formula (V) according to the reaction scheme below:

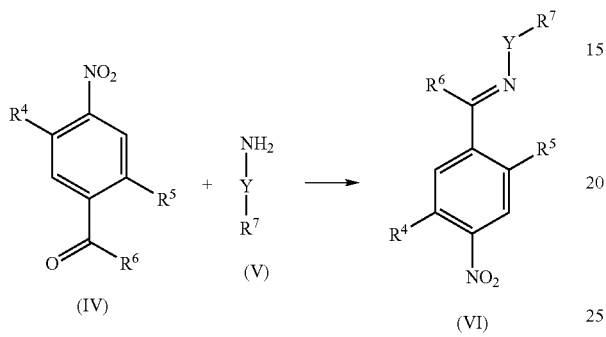

(b) reaction of aminobenzaldehydes or aminobenzoketones of the formula (VII) with amines of the formula (V) according to the reaction scheme below:

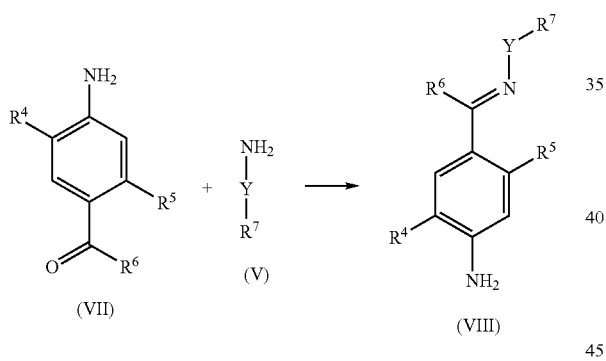

(c) reduction of the nitroaromatics of the formula (VI) to anilines of the formula (VIII) according to the reaction scheme below:

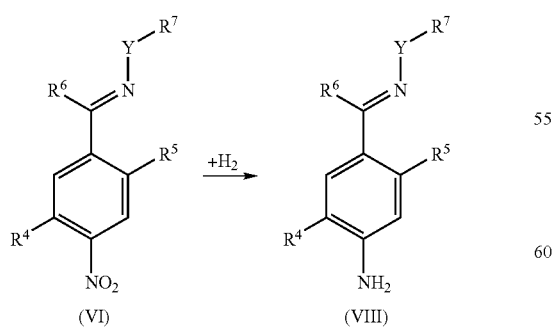

(d) reaction of the anilinoxime ethers of the formula (VIII) with
 (i) aminoacetals of the formula (XIII) or
 (ii) with amides of the formula (XIV) or
 (iii) with amines of the formula (XV) in the presence of ortho esters of the formula (XVI)
according to the reaction scheme below:

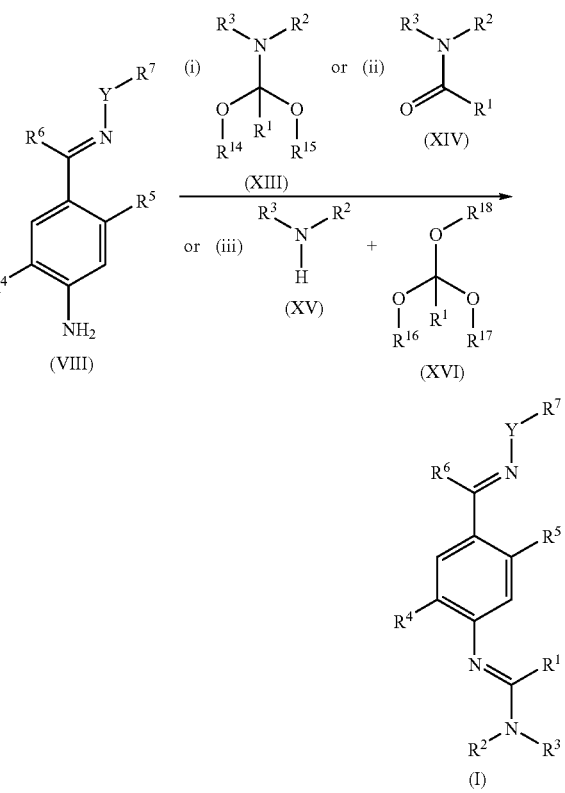

(e) reaction of the aminobenzaldehydes or aminobenzoketones of the formula (VII) with
 (i) aminoacetals of the formula (XIII) or
 (ii) with amides of the formula (XIV) or
 (iii) with amines of the formula (XV) in the presence of ortho esters of the formula (XVI)
according to the reaction scheme below:

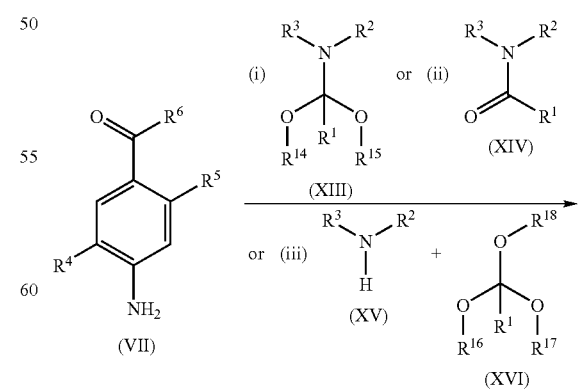

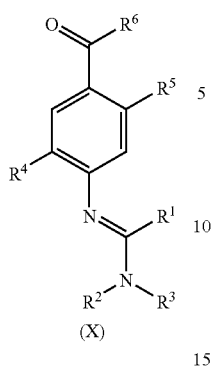

(X)

(f) reaction of amidines of the formula (X) with amines of the formula (V) according to the reaction scheme below:

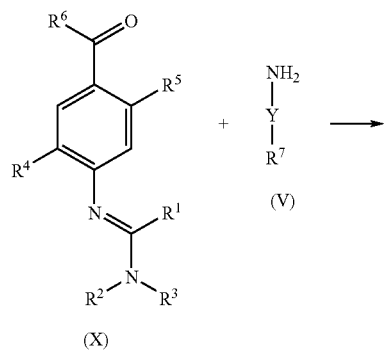

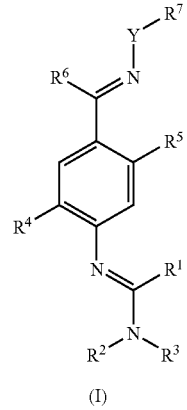

(I)

where in the above schemes
Y, $R^1$ to $R^{13}$ have the above meanings;
$R^{14}$ and $R^{15}$ independently of one another are selected from the group consisting of hydrogen, $C_{1-12}$-alkyl, $C_{2-12}$-alkenyl, $C_{2-12}$-alkynyl or $C_{5-18}$-aryl or $C_{7-19}$-arylalkyl groups and together with the oxygen atoms to which they are attached may form a five-, six- or seven-membered ring;
$R^{16}$, $R^{17}$ and $R^{18}$ independently of one another are selected from the group consisting of hydrogen, $C_{1-12}$-alkyl, $C_{2-12}$-alkenyl, $C_{2-12}$-alkynyl or $C_{5-18}$-aryl or $C_{7-19}$-arylalkyl, $C_{7-19}$-alkylaryl groups and in each case $R^{10}$ with $R^{12}$, $R^{10}$ with $R^{11}$ or $R^{11}$ with $R^{12}$ together with the oxygen atoms to which they are attached may form a five-, six- or seven-membered ring.

\* \* \* \* \*